United States Patent [19]

Previte

[11] 4,116,706
[45] Sep. 26, 1978

[54] ADDITIVE COMPOSITION FOR HYDRAULIC CEMENT COMPOSITIONS

[75] Inventor: Robert W. Previte, Lawrence, Mass.

[73] Assignee: W. R. Grace & Co., Cambridge, Mass.

[21] Appl. No.: 812,211

[22] Filed: Jul. 1, 1977

[51] Int. Cl.$^2$ ............................................. C04B 7/35
[52] U.S. Cl. .................................... 106/90; 106/315
[58] Field of Search ............................ 106/315, 90

[56] References Cited

U.S. PATENT DOCUMENTS

3,090,692  5/1963  Kelly et al. .......................... 106/315

*Primary Examiner*—James Poer
*Attorney, Agent, or Firm*—William L. Baker; C. Edward Parker

[57] ABSTRACT

An improved additive composition for accelerating the rate of hydration and increasing the compressive strength of hydraulic cement compositions such as Portland cement concrete contains a chloride, formate or nitrite salt set accelerator, an amine and a small amount of a certain select synthetic non-ionic surface active agent.

27 Claims, 2 Drawing Figures

ADDITIVE COMPOSITION FOR HYDRAULIC CEMENT COMPOSITIONS

FIELD OF THE INVENTION

This invention relates to improved additions for hydraulic cement compositions. More particularly, this invention pertains to an improved additive composition for especially Portland cement concretes, mortars, etc., designed to accelerate the rate of hydration particularly at low temperature and to increase the compressive strength of such cement compositions.

DESCRIPTION OF THE PRIOR ART

My previously filed copending application U.S. Ser. No. 744,465 filed Nov. 24, 1976 now abandoned, describes my discovery that certain members of the large group of synthetic surface active agents are particularly effective by themselves as very low addition rate additives to increase the extended compressive strength of hydrated hydraulic cement compositions such as Portland cement concrete, etc. More particularly, my previous application describes my discovery that certain synthetic organic compounds which are surface active, have only a low solubility in water, and further which exhibit a limited foaming ability will significantly enhance the extended or overall (28 day) compressive strength of the hydrated cement product at very low addition rates, i.e., when added in amounts of only about 0.001 to about 0.1% by weight based upon the cement. The surface-active additives I employ in such invention do not entrain air in the hydrated cement in amounts deleterious to compressive strength and thus are effective by themselves as strength-enhancing agents. One very desirable practical advantage offered by the use of the surfactant additives is that due to their low foamability and low water solubility, the danger of entraining unwanted high air contents in the cement product through an accidental overdose of the additive is considerably diminished.

As pointed out in my previous application U.S. Ser. No. 744,465, the select surfactant additives of my previous invention can be combined with any of the previously known cement additive materials in the art such as set-accelerating additive, supplemental compressive strength enhancing agents, etc, to give a single additive composition which affects several properties of the cement composition which is especially desirable from a commercial standpoint. Thus my application U.S. Ser. No. 744,465 describes an embodiment of my previous invention wherein the select surfactants are combined with calcium chloride which is a well known set-accelerating agent for Portland cement compositions, and as a supplemental compressive strength enhancing agent, corn syrup, previously employed in the art as a strength-enhancing additive material. This combination additive composition was generally successfully commercially applied as a set-accelerating, strength-enhancing additive for Portland cement concrete, particularly concrete intended to be placed at low ambient temperatures, i.e. 60° F. and below, under which low temperature conditions acceleration of the setting time is especially desired. However, a performance disadvantage evidenced in the application of such combination additive composition to Portland cement concrete was that the setting time of the concrete was not shortened at addition rates higher than those recommended.

SUMMARY OF THE INVENTION

This invention concerns a combination additive composition which makes use of the select compressive strength-enhancing surfactants of the type described in my previous application U.S. Ser. No. 744,465 and more particularly defined below and which also will act to shorten the setting time of hydraulic cement compositions such as Portland cement concrete, especially at low temperature. Unlike the prior art combination additive composition described above however, the degree of shortening of setting time (or "set-acceleration") obtained with the composition of this invention is proportional to the rate of addition of the composition to the cement composition. Thus an important advantage is obtained in that a reliable pre-determined degree of set-acceleration can be obtained by selecting the addition level in advance.

The set-accelerating, strength-enhancing additive composition of this invention comprises a set-accelerating amount of a chloride, formate or nitrite salt accelerator, or amine, preferably on alkanolamine, and a very small proportion of the select surface active agents described below.

DETAILED DESCRIPTION OF THE INVENTION INCLUDING THE ILLUSTRATIVE EMBODIMENTS

The accelerating component of the composition of the invention can be any of the chloride, formate or nitrite salts conventionally employed to accelerate the setting time of hydraulic cements. Calcium chloride is most often employed for this purpose. Calcium or amine formate as well as calcium nitrite are also aften used. The amount of accelerator employed will be generally a major proportion, that is, greater than 50% of the total additive composition, on a solids basis.

The amine component of the additive composition is also water-soluble and generally contains up to about 20 carbon atoms in their structural formula. Suitable amines for use in preparing the additive of the invention include primary, secondary and tertiary mono- and polyamines such as aliphatic, including cycloaliphatic, mono- and polyamines, for example, isopropylamine, n-propylamine, diisopropylamine, n-butylamine, di-n-butylamine, tri-n-butylamine, triethylamine, cyclohexylamine, ethylene diamine, diethylene triamine, triethylene tetramine, tetraethylene pentamine, etc,; heterocyclic N-containing mono- and polyamines, for example, morpholine, N-methylmorpholine, 4-(2-aminoethoxy) ethylmorpholine, 2-(4-morpholinylethoxy) ethanol, bis-2-(4-morpholinyl) ethyl ether, piperazine, N-aminoethylpiperazine, N-hydroxyethylpiperazine, pyridazine, pyrrole, pyrrolidine, pyridine, piperadine, pyrimidine, pyridazine, etc. Also suitable are alkanolamines such as triethanolamine. Mixtures of the foregoing amines, such as residue products resulting from the commercial production of pure or essentially pure amines are especially desirable for use in preparing the additive of the invention due to the relative low cost of such products. The amount of amine employed in the additive composition generally ranges between about 1 and 6 percent by weight of the additive composition (solids basis).

The strength-enhancing surface active agent component employed in the additive composition of the invention is as aforementioned one or more of those of the type described in my previous application U.S. Ser. No. 744,456 and described in detail below. Such materials are synthetic surfactants, that is, they reduce the surface tension of water or reduce interfacial tension between liquids or between a liquid and a solid. Further, the synthetic surfactant additives employed in my invention have only a low solubility in water as is evidenced by their having a limited cloud point value. The "cloud point" of surfactants is a term conventionally employed in the surfactant art. It is used to indicate the sudden onset of turbidity of surfactant solution on raising the temperature("NON-IONIC SURFACTANTS," Schick, Vol. 1, P. 571 (1967)). As used herein, the term indicates the temperature in degree centigrade at which a sudden onset of turbidity is observed in a 1% solution of the surfactant in water. I have found that this low solubility as indicated by cloud point is an important criterion in the ability of the surfactant to increase the compressive strength of hydraulic cements at low addition rates. Through my experiments with various synthetic surfactants, I have determined that useful surfactants according to my invention have cloud points which do not exceed about 80° C.

I have found further that surface activity and low water solubility are not the only important criteria in determining the usefulness of surfactants as low addition rate, strength-enhancing additives to hydraulic cements according to my invention. My experiments below with certain surfactants have further shown that they must also be low foam-producing, and I have found that this requisite low foaming property can be reliably assessed using a mechanically-induced, agitative foaming test developed by me.

In this test, the foaming ability of the surfactant is assessed by measuring the height of foam produced as the result of mechanical agitation at room temperature of a given amount of the surfactant dissolved or dispersed in a water, or a water-alcohol solution. The value obtained by the test procedure is termed herein and in the attached claims as the "mechanically-induced agitated foam height" of the surfactant.

This test procedure is best described in detail having reference to the accompanying drawings wherein.

Figure 1:
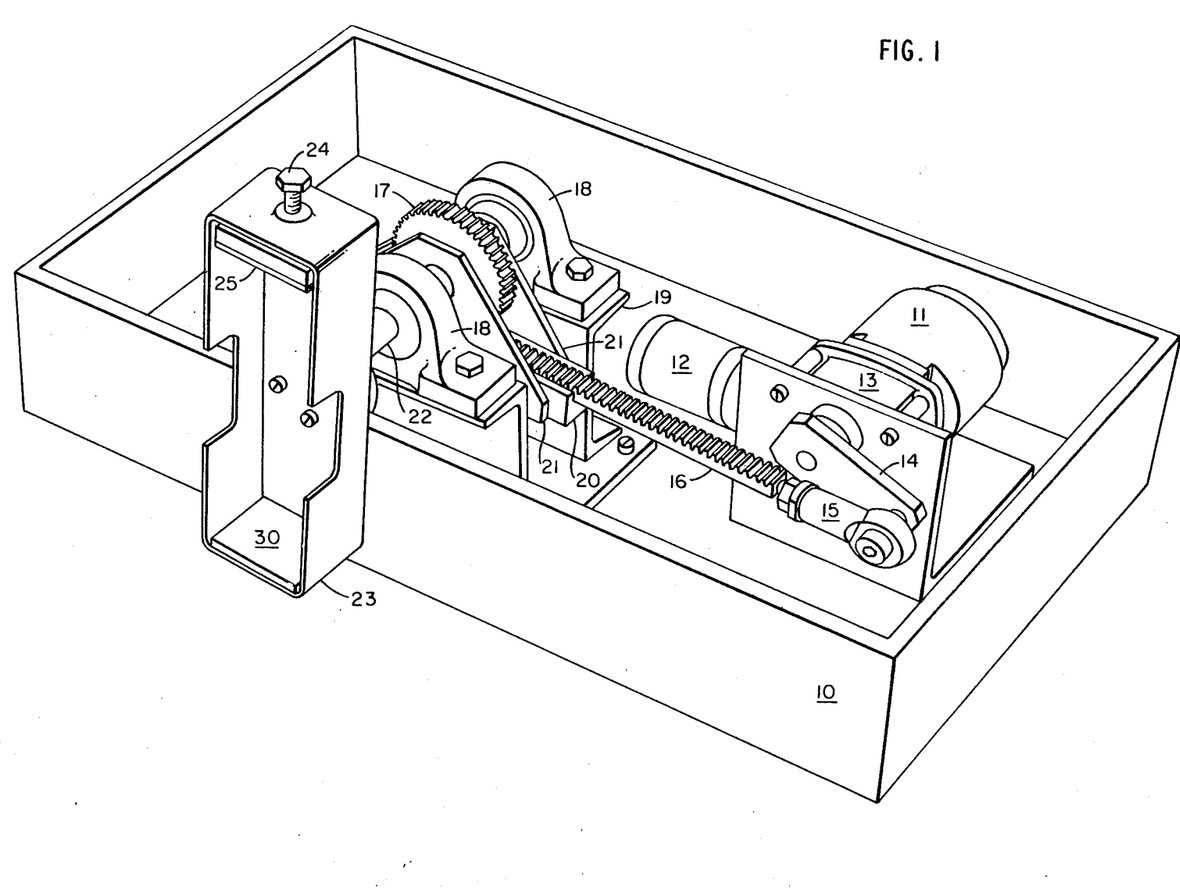
FIG. 1 is a perspective view of the mechanical apparatus for controlled agitation of the surfactant sample.

Referring now to FIG. 1, container 10 has mounted therein an electric speed reducer motor 11 (one seventy-fifth horsepower, 1800 rpm, 115 VAC) suitably wired through a capacitor 12 and linked to a gear reducer 13 (30/1 ratio output, 8.2 inch-pounds torque at 60 rpm). Both the motor and the gear reducer are products of the Bodine Electric Co., Chicago, Ill. The speed reducer 13 is connected to a crank arm 14 which in turn is pivotally attached to rack 16 through a ballend 15. The rotational motion of crank arm 14 is thus converted to a reciprocating, somewhat longitudinal, motion of rack 16 through this arrangement. Rack 16 cooperates with pinion gear 17, which is secured to shaft 22. Support frame 19 rigidly anchors a pair of ¾ inch journal bearings 18 to container 10. Shaft 22 is secured at one end to a housing 23 for the sample container, and then journaled through first bearing 18, a support 21 for rack 16, pinion gear 17, and at its opposite end through the second bearing 18. Rack 20 is free to pivot about shaft 22. Through this arrangement, the reciprocating motion of rack 20 is converted to an oscillatory motion of housing 23.

Housing 23 has a set screw 24 threaded through its upper end. The set screw is welded to a metal plate having a rubber pad 25 adhered to its surface. Rotation of screw 24 in turn raises or lowers the padded metal plate within the housing. Housing 23 has another rubber pad 30 at the bottom thereof.

Figure 2:
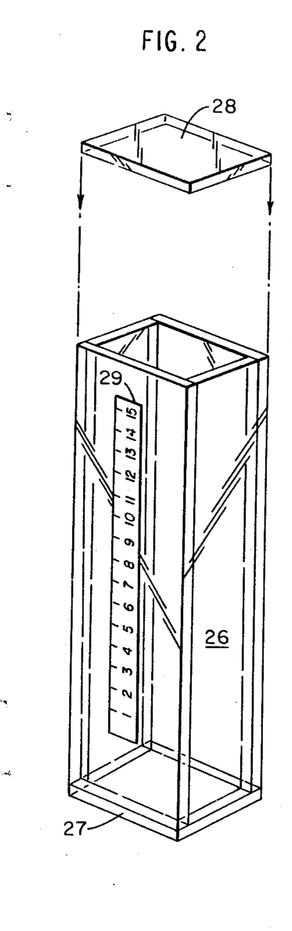
FIG. 2 is a perspective view of the ruled container used in the apparatus in which the surfactant sample is deposited and ensuing foam height measured.

The surfactant sample is held in a glass container shown in FIG. 2. Container 26 has four leak-proof glass sides and glass bottom 27. Ground glass top 28 is removable. A ruler 29 graduated in millimeters is taped to the outside of the container. The glass container is described in ASTM C115-73, section 2.2.4. It is rectangular as shown, having inside dimensions of 2 inches by 1½ inches by 8 inches in height.

Operation of the device is as follows. The surfactant sample to be tested is placed in container 26. Top 28 is then positioned in a fluid-tight manner, e.g., by first wetting the edge of container 26 contacting the ground glass top 28. The sealed container is then placed in housing 23 and the set screw 24 tightened to hold the glass container. Activation of motor 11 turns crank arm 14, which in turn causes rack 16 to move within slide 20. Movement of the rack causes pinion gear 17 to rotate one way, then another, which in turn oscillates housing 23 holding container 26. The device is constructed such that housing 23 inverts 180° about a horizontal axis through the center of the container 26, turning the container upside down and back again to its original upright position once each second of time.

"Mechanically induced agitated foam height" is calculated herein in the following manner. A 0.10% by weight solution of the surfactant in either (a) distilled water or (b) a mixture containing 95% by weight distilled water and 5% by weight isopropyl alcohol (Fisher Scientific Co. Catalogue No. A-419, Certified A.C.S. Spectranalized 2-Propanol) is prepared. A ruler graduated in millimeters is affixed to the outside of the glass container such that the zero point of the ruler is exactly at the height of 100 millimeters of a liquid placed therein (measured at the meniscus of the liquid). 100 milliliters of the aforementioned surfactant solution is pipetted into the container, and the container secured in the housing 23. The container is agitated for 5 minutes. After one minute has elapsed following cessation of the agitation, the height of the foam produced is measured. An "Individual Value" is recorded which is an average of the height across the entire surface of the foam produced. The sample is discarded and the entire procedure may be repeated one or more times, the final recorded value in the case of multiple readings being an "Average Foam Height", an actual numerical average of the "Individual Values."

My experiments with the synthetic surfactants below have shown that in addition to surface-activity and low solubility as indicated by the limited cloud point value mentioned previously, synthetic surfactants for use according to the invention are those which in addition exhibit mechanically-induced agitated average foam height values of less than about 30 millimeters when tested as above as a 0.10% by weight solution both in (a) distilled water alone and in (b) the aforementioned water-alcohol mixture. If the surfactant exhibits a foam height in excess of about 30 millimeters when tested as such a solution in either (a) or (b) it is likely to entrain strength-damaging amounts of air in cement compositions.

While both ionic and non-ionic surface active agents have been tested for strength enhancement in concrete in my experiments, the majority of my experimental work has been with synthetic surface active agents of the non-ionic type. Synthetic non-ionic surface active agents are well known in the art. They are characterized as exhibiting no ionic charge in aqueous solution. Hydrophilic character is often due to the presence of ether linkage, hydroxy groups, etc. in the molecule. All of the non-ionic surface active agents found useful for purposes of my invention are commercially available products.

Illustrative of the synthetic non-ionic low addition rate strength enhancing surfactants preferred for use in my invention are those members meeting the aforementioned low solubility and low foamability requirements and belonging to such classes as:

(a) Alkyl aryl polyether alcohols such as the condensation products of alkylphenols, e.g. octylphenol and nonylphenol, with alkylene oxides, e.g. ethylene oxide; exemplary members of this group found useful according to the invention include condensation products of octylphenol and nonylphenol having a particular degree of exthoxylation and offered commercially, for example, under the tradenames "Triton," "IGEPAL CO," and "Surfonic N";

(b) Block copolymers of alkylene glycols or alkylene diamines and one or more alkylene oxides, such as those prepared by the sequential addition of propylene oxide and then ethylene oxide to a propylene glycol nucleus, or by the sequential addition of ethylene oxide and then propylene oxide to an ethylene glycol base or to the diamine base; exemplary members of this group found useful according to this invention include certain block copolymers of propylene glycol, propylene oxide and ethylene oxide offered commercially under the tradenames "Pluronic," and "Pluronic R"; and "Tetronic."

(c) Acetylenic glycols and reaction products thereof with alkylene oxides such as ethylene oxide; exemplary members of this group found useful herein include tertiary acetylenic glycols offered commercially under the tradenames "Surfynol 104" and certain condensation product thereof prepared by reacting such with ethylene oxide and offered commercially under the tradenames "Surfynol 440" and "Surfynol 465."

The previously defined surfactants are effective in the compositions of the invention in only very small amounts, generally in the range of only about 0.15 to about 3 percent by weight of the composition, preferably about 0.50 to about 1 percent on a solids basis.

The additives according to my invention are particularly valuable for decreasing the setting time, increasing the early compressive strength as well as extended compressive strength of Portland cement compositions, especially Portland cement concrete. Portland cement is by far the most widely used hydraulic cement. The term "hydraulic cement" as employed herein includes those inorganic cements which, when mixed with water, set and harden as a result of chemical reactions between the water and the compounds present in the cement. Organic "glues," pastes, etc., are not included within this definition. The term "Portland cements" as employed herein include those products prepared by heating a mixture of limestone and clay or shale, or other calcareous and argillaceous materials to a fused state. The fused product, which is called clinker, is interground with a few percent, normally about 4 to 6 percent, of a retarder such as gypsum.

The term "concrete" as used herein includes a mixture of such hydraulic cements and inert aggregates. Typical aggregates include conventional "coarse" aggregates such as gravel, granite, limestone, quartz sieve, etc., as well as those materials conventionally referred to as "fine" aggregates such as sand and fly ash. Conventional hydraulic cement concretes, e.g. Portland cement concretes, employ major amounts, i.e. over 50%, usually up to about 75% by volume of such aggregates in the set product.

The additives of the invention are especially suited for use in concretes intended for structural uses where high compressive strengths are particularly sought. These concrete compositions employ water to cement ratios of less than 1, usually from about 0.4 to about 0.6, and when hardened have compressive strength values typically in excess of 2000 psi after 28 days of preparation.

The compositions of the invention can include conventional additional optional additives not specified already, but do not include materials which deleteriously affect the extended strengths such as strength-diminishing amounts of petroleum or other hydrocarbon oils, air-entraining agents, etc.

The term "consisting essentially of" as employed herein and in the claims to define the compositions of the invention is intended as inclusive of those ingredients specifically mentioned herein as well as any additional unspecified conventional ingredients, but is intended to be exclusive of additional unspecified ingredients in amounts which deleteriously affect the extended or overall compressive strength of the set compositions.

In my experiments described below, Portland cements from various manufacturers were employed to make hydratable compositions. The cements all met ASTM standards for Portland cements. Where employed, the concrete compositions were prepared according to ASTM C494 test procedures unless noted otherwise. Determinations of the amount of air entrained in the hydrated samples produced in the experiments below were made according to ASTM test procedure No. C231. Also, the "slump" of the wet mixes produced in the experiments was determined according to ASTM test procedure No. C143. This is a measure of the relative consistency or plasticity of the wet mix. The compressive strength of the mixes given below was determined by preparing test specimens and curing in accordance with ASTM procedure No. C192. The compressive strengths of the specimens were measured after 1, 7 and 28 days in accordance with ASTM C39.

The Examples below are representative of the results I have obtained from a number of actual experiments testing the effect of the specific surfactants listed in Portland cement compositions. They are intended as illustrative only of my invention.

EXAMPLE I

This example illustrates the effect of small amounts of various commercially produced synthetic non-ionic polyol surfactants sold commercially by the WYANDOTTE CHEMICALS CORP. under the trademark "Pluronic," upon the air content and compressive strength of Portland cement concretes. As aforementioned, the concretes in this and later Examples, were prepared in accordance with ASTM procedures, and measurements of the water to cement ratio, slump, air content and compressive strengths of the hydrated concretes made in each case were also made using ASTM procedures. For comparison, a "blank" containing no additive was identically prepared and tested. As will be understood by one skilled in the art, measurements are first made with respect to the "blank" composition. The compositions containing the surfactant additives are then prepared and sufficient water added to the mix to give a "slump" as close as possible to that exhibited by the blank, plus or minus about ½ inch. The amount of water actually used is recorded for calculation of the W/C ratio, and subsequently air content and compressive strengths at 1, 7 and 28 days are measured.

The "Pluronic" polyols employed herein have been fully described in the literature. They are 100% active, non-ionic block copolymers made by controlled addition of propylene oxide to the two hydroxyl groups of a propylene glycol nucleus. The resulting hydrophobe can be tailored to any desired length, varying from 800 to several thousands in molecular weight. The customized addition of ethylene oxide to this hydrophobe "sandwiches" it between hydrophilic poly (oxyethylene) groups of controlled length constituting from 10 to 80% of the final molecule. The nomenclature of the "Pluronic" materials employed herein is that of the manufacturer.

The "Pluronic R" surfactants employed herein are similar to the aforedescribed "Pluronic" materials. They are also non-ionic block copolymers, but the copolymer structure is reversed. They are prepared by the sequential addition of ethylene oxide and then propylene oxide to an ethylene glycol base. The copolymer again contains a hydrophobic polyoxypropylene portion and a hydrophilic polyoxyethylene portion. Specific details concerning the chemical nature of the "Pluronic" and "Pluronic R" materials are given in Table I below, and the aforementioned effects of such on Portland cement concretes are shown in Tables II–IX. In these and all the Tables following, the manufacturer and the ASTM type of the cement used is given. Also, the percentage addition rate for the additive shown in the Tables is that as calculated based on the weight of the cement solids (solids on solids).

TABLE I

| "Pluronic" Product Designation | Typical Molecular Wt. of Poly (oxy propylene) Hydrophobe | % Poly (oxyethylene) Hydrophilic Unit in total Molecule |
|---|---|---|
| L31 | 950 | 10 |
| L35 | 950 | 50 |
| L42 | 1200 | 20 |
| L43 | 1200 | 30 |
| L44 | 1200 | 40 |
| L61 | 1750 | 10 |
| L62 | 1750 | 20 |
| L63 | 1750 | 30 |
| L72 | 2050 | 20 |
| L81 | 2250 | 10 |
| P84 | 2250 | 40 |
| L92 | 2750 | 20 |
| L101 | 3250 | 10 |
| P103 | 3250 | 30 |
| P104 | 3250 | 40 |
| P105 | 3250 | 50 |
| F108 | 3250 | 80 |
| L121 | 4000 | 10 |
| L122 | 4000 | 20 |
| P123 | 4000 | 30 |
| F127 | 4000 | 70 |
| 25R1 | 2500 | 10 |
| 31R1 | 3100 | 10 |
| 25R2 | 2500 | 20 |
| 31R2 | 3100 | 20 |
| 25R4 | 2500 | 40 |
| 31R4 | 3100 | 40 |
| 25R8 | 2500 | 80 |

TABLE II

CANADA I CEMENT BATCH A

| PLURONIC Polyol (0.02%) | W/C | Slump | % Air | COMPRESSIVE STRENGTH - PSI | | |
|---|---|---|---|---|---|---|
| | | | | 1 Day | 7 Days | 28 Days |
| Blank | 0.59 | 3¾ | 1.9 | 1023 | 3175 | 4130 |
| L-81 | 0.58 | 3¾ | 2.2 | 1230 | 3537 | 4524 |
| L-92 | 0.56 | 3 | 2.6 | 1321 | 3684 | 4627 |
| L-62 | 0.56 | 3¼ | 2.5 | 1484 | 3959 | 4799 |
| L-63 | 0.55 | 3 | 2.8 | 1428 | 3684 | 4695 |
| P-103 | 0.48 | 4 | 7.2 | 1421 | 3418 | 4190 |

CANADA I CEMENT BATCH B

| Blank | 0.60 | 4¼ | 2.0 | 1098 | 3247 | 4468 |
|---|---|---|---|---|---|---|
| P-105 | 0.48 | 5 | 8.8 | 1046 | 2646 | 3410 |

TABLE III

ATLANTIC I CEMENT BATCH C

| PLURONIC Polyol (0.05%) | W/C | Slump | % Air | COMPRESSIVE STRENGTH - PSI | | |
|---|---|---|---|---|---|---|
| | | | | 1 Day | 7 Days | 28 Days |
| Blank | 0.60 | 4¼ | 1.4 | 1098 | 2909 | 3907 |
| L-81 | 0.57 | 4¼ | 1.9 | 1261 | 3207 | 4504 |
| L-92 | 0.51 | 3¾ | 4.0 | 1572 | 3645 | 4803 |
| L-62 | 0.55 | 4 | 2.7 | 1361 | 3426 | 4397 |
| L-63 | 0.55 | 4¼ | 2.9 | 1337 | 3346 | 4592 |
| L-44 | 0.55 | 4 | 3.6 | 1293 | 3318 | 4345 |
| L-35 | 0.55 | 4¼ | 4.0 | 1234 | 3116 | 4218 |
| P-103 | 0.46 | 6 | 12.7 | 875 | 2053 | 2566 |
| F-127 | 0.45 | 5¼ | 13.8 | 764 | 1600 | 2033 |
| F-108 | 0.46 | 5¼ | 13.0 | 772 | 1986 | 2324 |

TABLE IV

ATLANTIC I CEMENT BATCH D

| PLURONIC Polyol (0.05%) | W/C | Slump | % Air | COMPRESSIVE STRENGTH - PSI | | |
|---|---|---|---|---|---|---|
| | | | | 1 Day | 7 Days | 28 Days |
| Blank | 0.60 | 4¼ | 1.4 | 1297 | 2753 | 4146 |
| L-62 | 0.57 | 4¼ | 2.5 | 1329 | 3131 | 4309 |
| L-63 | 0.57 | 4¼ | 2.8 | 1289 | 3048 | 4381 |
| L-44 | 0.56 | 5 | 3.4 | 1421 | 3227 | 4361 |
| P-84 | 0.46 | 5¼ | 10.1 | 1373 | 2646 | 3696 |
| L-35 | 0.56 | 4¼ | 3.1 | 1397 | 3203 | 4261 |
| P-104 | 0.44 | 6¼ | 14.7 | 557 | 1202 | 1556 |
| P-103 | 0.44 | 4¼ | 9.6 | 1393 | 2785 | 3493 |
| P-123 | 0.48 | 4¾ | 9.0 | 1313 | 2646 | 3322 |

TABLE V

ATLANTIC I CEMENT BATCH E

| PLURONIC R Polyols | W/C | Slump | % Air | COMPRESSIVE STRENGTH - PSI | | |
|---|---|---|---|---|---|---|
| | | | | 1 Day | 7 Days | 28 Days |
| Blank | 0.61 | 3¾ | 1.6 | 1011 | 2976 | 4425 |
| 0.05% 31 R1 | 0.57 | 3¼ | 2.5 | 1114 | 3697 | 4818 |
| 0.05% 31 R2 | 0.57 | 4 | 2.7 | 1051 | 3478 | 4683 |
| 0.05% 25 R1 | 0.57 | 4 | 2.6 | 1067 | 3486 | 4783 |
| 0.05% 25 R2 | 0.57 | 3¼ | 2.5 | 1166 | 3796 | 4990 |
| 0.05% 25 R8 | 0.57 | 3¼ | 2.8 | 1043 | 3549 | 4846 |
| 0.05% 31 R4 | 0.56 | 3 | 2.9 | 1126 | 3462 | 4970 |
| 0.05% 31 R4 | 0.57 | 4¼ | 3.3 | 1015 | 3418 | 4747 |
| 0.05% 25 R4 | 0.57 | 4¼ | 3.2 | 999 | 3438 | 4679 |

CANADA I CEMENT BATCH E'

| Blank | 0.60 | 4¼ | 1.6 | 1130 | 2264 | 4329 |
|---|---|---|---|---|---|---|
| Blank | 0.59 | 3¾ | 1.9 | 859 | 1934 | 3497 |
| 0.01% 25 R1 | 0.57 | 3¾ | 2.2 | 1289 | 2519 | 4616 |
| 0.01% 25 R2 | 0.57 | 3¾ | 2.3 | 1381 | 2586 | 4616 |

UNIVERSAL ATLAS INDIANA I CEMENT BATCH E"

| Blank | 0.60 | 4 | 1.4 | 784 | 3358 | 5181 |
|---|---|---|---|---|---|---|
| 0.01% 35 R1 | 0.58 | 3¼ | 2.3 | 870 | 3633 | 5368 |
| 0.01% 35 R2 | 0.58 | 3¾ | 2.1 | 875 | 3848 | 5376 |
| 0.01% 31 R4 | 0.57 | 3 | 2.4 | 1011 | 3935 | 5805 |

TABLE VI

ATLANTIC I CEMENT BATCH F

| PLURONIC L92 | W/C | Slump | % Air | 1 Day | 7 Days | 28 Days |
|---|---|---|---|---|---|---|
| | | | | | COMPRESSIVE STRENGTH - PSI | |
| Blank | 0.60 | 4¾ | 1.4 | 1162 | 2745 | 4150 |
| 0.001% | 0.58 | 4¼ | 2.2 | 1186 | 3000 | 4281 |
| 0.005% | 0.56 | 4¼ | 2.6 | 1452 | 3410 | 4584 |
| 0.010% | 0.56 | 3¼ | 2.6 | 1444 | 3394 | 4639 |
| 0.010% | 0.56 | 5¼ | 2.7 | 1170 | 3076 | 4301 |
| 0.025% | 0.54 | 4¼ | 3.2 | 1249 | 3199 | 4675 |
| 0.050% | 0.52 | 5 | 5.5 | 1448 | 3159 | 4126 |
| 0.100% | 0.49 | 6¼ | 8.9 | 1281 | 2773 | 3768 |

TABLE VII

CANADA I CEMENT BATCH G

| PLURONIC Polyol | W/C | Slump | %Air | 1 Day | 7 Days | 28 Days |
|---|---|---|---|---|---|---|
| | | | | | COMPRESSIVE STRENGTH - PSI | |
| Blank | 0.60 | 3½ | 1.8 | 1154 | 3183 | 4389 |
| 0.02% L-121 | 0.58 | 4½ | 1.9 | 1257 | 3557 | 4652 |
| 0.04% L-121 | 0.58 | 3 | 1.9 | 1277 | 3772 | 4735 |
| 0.02% L-101 | 0.58 | 4 | 1.9 | 1297 | 3597 | 4540 |
| 0.04% L-101 | 0.58 | 3 | 1.7 | 1289 | 3529 | 4719 |
| 0.02% L-81 | 0.57 | 3½ | 2.0 | 1110 | 3454 | 4532 |
| 0.04% L-81 | 0.58 | 3¾ | 1.8 | 1226 | 3700 | 4687 |
| 0.02% L-61 | 0.57 | 3½ | 2.1 | 1134 | 3482 | 4472 |
| 0.04% L-61 | 0.57 | 4¼ | 2.0 | 1353 | 3617 | 4974 |

CANADA I CEMENT BATCH H

| | W/C | Slump | %Air | 1 Day | 7 Days | 28 Days |
|---|---|---|---|---|---|---|
| Blank | 0.60 | 4 | 1.6 | 1158 | 3243 | 4544 |
| 0.01% L-122 | 0.57 | 3¼ | 2.3 | 1337 | 3549 | 4651 |
| 0.02% L-122 | 0.57 | 5 | 3.8 | 1297 | 3493 | 4548 |
| 0.04% L-122 | 0.57 | 4½ | 3.1 | 1421 | 3688 | 4743 |
| 0.01% L-92 | 0.57 | 4¾ | 2.6 | 1309 | 3577 | 4787 |
| 0.02% L-92 | 0.55 | 3¼ | 3.1 | 1417 | 3800 | 4918 |
| 0.04% L-92 | 0.51 | 4 | 5.3 | 1345 | 3490 | 4417 |

TABLE VIII

IDEAL I CEMENT BATCH I

| PLURONIC Polyol | W/C | Slump | % Air | 1 Day | 7 Days | 28 Days |
|---|---|---|---|---|---|---|
| | | | | | COMPRESSIVE STRENGTH - PSI | |
| Blank | 0.59 | 4¼ | 1.4 | 1122 | 3275 | 5073 |
| 0.04%L92 | 0.56 | 4¼ | 1.8 | 1273 | 3553 | 5595 |
| 0.04%L92 | 0.57 | 3¾ | 1.9 | 1202 | 3760 | 5734 |
| 0.08%L92 | 0.56 | 3¼ | 2.0 | 1241 | 3649 | 5730 |

ATLANTIC I CEMENT BATCH J

| Blank | 0.60 | 4¼ | 1.3 | 1170 | 3227 | 4795 |
|---|---|---|---|---|---|---|
| 0.05%L92 | 0.57 | 3¾ | 2.2 | 1281 | 3601 | 5344 |

ATLANTIC I CEMENT BATCH K

| Blank | 0.60 | 4 | 1.3 | 1114 | 3418 | 4942 |
|---|---|---|---|---|---|---|
| 0.001%L92 | 0.58 | 4¼ | 1.8 | 1289 | 3728 | 5005 |
| 0.005%L92 | 0.56 | 3¼ | 2.1 | 1472 | 3716 | 5181 |
| 0.010%L92 | 0.57 | 4¼ | 1.9 | 1345 | 3720 | 5097 |
| 0.050%L92 | 0.56 | 4¼ | 2.2 | 1389 | 4039 | 5387 |
| 0.100%L92 | 0.55 | 3¾ | 2.1 | 1421 | 4162 | 5527 |

CANADA I CEMENT BATCH L

| Blank | 0.59 | 4¼ | 2.3 | 908 | 2905 | 3907 |
|---|---|---|---|---|---|---|
| 0.10%L92 | 0.52 | 5 | 5.8 | 1146 | 3092 | 3935 |

IDEAL I CEMENT BATCH M

| Blank | 0.57 | 4¼ | 1.5 | 1214 | 3744 | 5368 |
|---|---|---|---|---|---|---|
| 0.005%L92 | 0.55 | 4¼ | 2.3 | 1202 | 3923 | 5547 |
| 0.010%L92 | 0.54 | 3¼ | 2.3 | 1174 | 4074 | 5630 |
| 0.050%L92 | 0.55 | 4¼ | 2.1 | 1162 | 4007 | 5718 |
| 0.10%L92 | 0.55 | 4¼ | 2.0 | 1162 | 4230 | 5809 |

UNIVERSAL ATLAS INDIANA I CEMENT BATCH N

| Blank | 0.58 | 4¼ | 1.3 | 863 | 3398 | 5025 |
|---|---|---|---|---|---|---|
| 0.005%L92 | 0.56 | 3¼ | 2.3 | 991 | 3947 | 5447 |
| 0.010%L92 | 0.55 | 3¼ | 2.2 | 1027 | 3772 | 5403 |
| 0.050%L92 | 0.55 | 3¼ | 2.3 | 991 | 3780 | 5395 |
| 0.100%L92 | 0.55 | 4 | 2.1 | 895 | 3573 | 5145 |

ATLANTIC I CEMENT* BATCH O

| PLURONIC Polyol | W/C | Slump | % Air | 1 Day | 7 Days | 28 Days |
|---|---|---|---|---|---|---|
| | | | | | COMPRESSIVE STRENGTH - PSI | |
| Blank | 0.60 | 4¼ | 1.2 | 1074 | 3052 | 4480 |
| 0.005%L92 | 0.56 | 4 | 2.1 | 1301 | 3490 | 5196 |
| 0.010%L92 | 0.56 | 4¼ | 2.3 | 1373 | 3525 | 5145 |
| 0.050%L92 | 0.55 | 4 | 2.4 | 1381 | 3669 | 5204 |

IDEAL I CEMENT BATCH P

| Blank | 0.57 | 4 | 1.6 | 1086 | 3279 | 5033 |
|---|---|---|---|---|---|---|
| 0.0025%L92 | 0.55 | 4 | 2.0 | 1261 | 3971 | 5447 |
| 0.005%L92 | 0.54 | 3¼ | 2.2 | 1265 | 4043 | 5686 |
| 0.010%L92 | 0.55 | 4¼ | 2.5 | 1321 | 3939 | 5797 |

*Different Lot from Batch J and K.

TABLE IX

ATLANTIC I CEMENT BATCH O

| PLURONIC Polyol | W/C | Slump | % Air | 1 Day | 7 Days | 28 Days |
|---|---|---|---|---|---|---|
| | | | | | COMPRESSIVE STRENGTH - PSI | |
| Blank | 0.61 | 3¾ | 1.5 | 840 | 3068 | 4699 |
| 0.02% L31 | 0.57 | 3 | 2.8 | 1035 | 3454 | 5372 |
| 0.02% L62 | 0.56 | 2¼ | 2.9 | 1050 | 3537 | 5244 |

CANADA I CEMENT BATCH R

| Blank | 0.59 | 3¼ | 1.9 | 1170 | 3326 | 4337 |
|---|---|---|---|---|---|---|
| 0.02% L72 | 0.56 | 3¼ | 2.3 | 1428 | 3812 | 4799 |
| 0.02% L92 | 0.54 | 3 | 3.4 | 1432 | 3915 | 4727 |
| 0.02% L43 | 0.56 | 2¼ | 2.6 | 1281 | 3577 | 4504 |

CANADA I CEMENT BATCH S

| Blank | 0.61 | 4¼ | 1.4 | 1110 | 3271 | 4409 |
|---|---|---|---|---|---|---|
| 0.01% L92 | 0.57 | 4¼ | 2.2 | 1245 | 3796 | 4986 |
| 0.01% L42 | 0.58 | 3¼ | 2.1 | 1281 | 3486 | 4747 |
| 0.01% L62 | 0.57 | 4 | 2.0 | 1329 | 3609 | 4651 |
| 0.01% L72 | 0.58 | 4¼ | 2.0 | 1192 | 3458 | 4528 |
| 0.01% L122 | 0.57 | 4¼ | 2.2 | 1285 | 3812 | 4440 |
| 0.005% L122 | 0.58 | 4 | 1.9 | 1230 | 3438 | 4532 |

CANADA I CEMENT BATCH T

| Blank | 0.60 | 3¾ | 1.6 | 1134 | 3350 | 4417 |
|---|---|---|---|---|---|---|
| 0.02% L61 | 0.58 | 3¼ | 1.8 | 1381 | 3593 | 4803 |
| 0.02% L62 | 0.57 | 3¼ | 2.1 | 1452 | 3752 | 4767 |
| 0.02% L63 | 0.57 | 3¼ | 2.1 | 1333 | 3525 | 4755 |
| 0.02% L43 | 0.57 | 3¼ | 2.3 | 1202 | 3358 | 4512 |
| 0.02% L42 | 0.57 | 3¼ | 2.3 | 1241 | 3346 | 4452 |
| 0.02% L31 | 0.58 | 4¼ | 2.2 | 1142 | 3386 | 4257 |

The total data I have gathered from all of my experiments with the "Pluronic" polyol additives has led me to exclude the Pluronic block copolymers "P-84"; "P-103"; "P-104"; "P-105"; "F-108"; "P-123"; and "F-127" as low addition rate strength-enhancing additives for hydraulic cement compositions. These materials, I have found, when added in an amount within the range of 0.001 to about 0.1 tend to cause relatively large amounts of incremental air to be entrained in the hydrated cement compositions and have no, or a negative effect on compressive strength development. My preferred block copolymer additives according to the invention are those designated Pluronic "L-62"; "L-72"; and "L-92"; since I have found that these gave optimum compressive strength increase most consistently. The useful "Pluronic" type block copolymer additives, that is, those prepared by adding propylene oxide to propylene glycol, followed by the addition of ethylene oxide as additives according to my invention appear to be those wherein (A) the typical molecular weight of the poly-(oxypropylene) hydrophobe is from about 950 to about 1750 and the % poly (oxyethylene) in the total molecule is from about 10 to about 50; or (B) wherein such molecular weight is from about 1750 to about 2750 and such % poly (oxyethylene) is from about 10 to about 30; or (C) wherein such molecular weight is from about 2750 to about 4000 and such % poly (oxyethylene) is from about 10 to about 20. Mixtures of such copolymers selected from such groups (A), (B), and (C) can also obviously be employed herein. The preferred such "Pluronic" type additives would appear to be those wherein the typical molecular weight of poly(oxyethylene) hydrophobe ranges from about 1450 to about 3000, and further wherein the % poly (oxyethylene) in the total molecule ranges between about 15 and about 35.

Further representative experimental data on the effects of such preferred "Pluronic" block copolymers as additives according to the invention are illustrated in Table X below.

TABLE X

UNIVERSAL ATLAS INDIANA I CEMENT BATCH U

| PLURONIC Polyol | W/C | Slump | % Air | 1 Day | 7 Days | 28 Days |
|---|---|---|---|---|---|---|
| Blank | 0.60 | 3¾ | 1.5 | 871 | 3748 | 5324 |
| 0.02% L62 | 0.56 | 3¼ | 2.9 | 887 | 3740 | 5328 |
| 0.02% L62 | 0.57 | 5 | 3.0 | 987 | 3999 | 5571 |
| 0.02% L72 | 0.57 | 3½ | 2.4 | 931 | 4074 | 5563 |
| 0.02% L92 | 0.55 | 4 | 2.7 | 859 | 3680 | 5742 |

UNIVERSAL ATLAS INDIANA I CEMENT BATCH V

| Blank | 0.60 | 4 | 1.4 | 744 | 3474 | 5356 |
|---|---|---|---|---|---|---|
| 0.02% L62 | 0.57 | 2¾ | 2.7 | 883 | 3983 | 5837 |
| 0.02% L72 | 0.57 | 3¾ | 2.8 | 816 | 3864 | 5471 |

UNIVERSAL ATLAS INDIANA I CEMENT BATCH W

| Blank | 0.60 | 3¾ | 1.4 | 788 | 3545 | 5097 |
|---|---|---|---|---|---|---|
| 0.02% L62 | 0.57 | 3¾ | 3.0 | 919 | 3784 | 5527 |
| 0.02% L72 | 0.57 | 4¼ | 2.5 | 883 | 3724 | 5571 |
| 0.02% L92 | 0.57 | 3¾ | 2.9 | 891 | 3716 | 5423 |

ATLANTIC I CEMENT BATCH X

| Blank | 0.60 | 4 | 1.4 | 1074 | 3529 | 4902 |
|---|---|---|---|---|---|---|
| 0.02% L62 | 0.56 | 3 | 2.6 | 1237 | 4003 | 4998 |
| 0.02% L72 | 0.57 | 3¾ | 2.4 | 1090 | 3704 | 4964 |
| 0.02% L92 | 0.57 | 4¼ | 2.8 | 1039 | 3796 | 5073 |

CANADA I CEMENT BATCH Y

| Blank | 0.60 | 4¼ | 1.6 | 1015 | 3123 | 4361 |
|---|---|---|---|---|---|---|
| 0.02% L62 | 0.58 | 4¼ | 2.7 | 1166 | 3561 | 4739 |
| 0.02% L72 | 0.57 | 3½ | 2.4 | 1281 | 3700 | 4830 |
| 0.02% L72 | 0.58 | 3½ | 2.7 | 1158 | 3374 | 4568 |
| 0.02% L92 | 0.57 | 4¼ | 3.3 | 1150 | 3677 | 4476 |
| 0.01% L92 | 0.57 | 5¼ | 2.4 | 1054 | 3167 | 3987 |
| 0.005% L92 | 0.58 | 4¼ | 2.0 | 1054 | 3235 | 4285 |
| 0.02% L42 | 0.58 | 4¾ | 2.5 | 1226 | 3700 | 4345 |

All of the "Pluronic R" type polyol block copolymers I have tested have been found useful as additive components according to my invention. However, the use of "Pluronic 25R8" as a strength-enhancer is extremely doubtful, as further tests with this material do not confirm the results of the experiment shown in Table V, as strength-damaging high air was entrained with this material in the further tests. This is to be expected as it is near the cloud point borderline of about 80° C. that I have chosen as a limit. The "Pluronic R" types used in my invention include materials wherein the typical molecular weight of the poly (oxypropylene) hydrophobe was about 2500 and % poly (oxyethylene) units was in the range of about 10 to 80, and materials wherein the such typical molecular weight was about 3100 and such % poly (oxyethylene) was about 10-40.

Table XI below lists each of the polyol block copolymers shown in Table I with its corresponding "cloud point," "surface tension," and "mechanically-induced, agitated foam height" values tested in water-alcohol mixture as previously described. In Table XI, the "Number of Tests" associated with the "Average Foam Height" is the actual number of tests performed on each sample, the individual values of which were averaged in accordance with the procedure described above.

TABLE XI

| Pluronic Polyol | Cloud Point (C°) | Surface Tension (Dynes/cm) | Mechanically-Induced, Agitated Foam Height | |
|---|---|---|---|---|
| | | | No. of Tests | Average foam Height (mm) |
| P-104 | 81 | 38.5 | 2 | 62 |
| P-105 | 91 | 40.8 | 2 | 83 |
| F-108 | >100 | 45.5 | 2 | 124 |
| P-123 | 90 | 34.3 | 2 | 57 |
| F-127 | >100 | 41.8 | 2 | >150 |
| P-103 | 86 | 37.6 | 2 | 47 |
| P-84 | 74 | 44.9 | 2 | 32 |
| L-63 | 34 | 45.9 | 2 | 24 |
| L-122 | 19 | 33.7 | 2 | 27 |
| L-42 | 37 | 49.5 | 4 | 8 |
| 25 R4 | 40 | 42.6 | 3 | 10 |
| 25 R8 | 80 | 50.8 | 4 | 9 |
| 31 R4 | 31 | 44.4 | 2 | 18 |
| L-43 | 42 | 50.3 | 2 | 7 |
| L-72 | 25 | 42.9 | 2 | 11 |
| L-62 | 32 | 45.3 | 2 | 16 |
| L-92 | 26 | 37.8 | 2 | 15 |
| L-61 | 24 | 43.5 | 2 | 6 |
| L-101 | 15 | 34.9 | 2 | 5 |
| 25 R1 | 28 | 41.0 | 2 | 10 |
| 31 R1 | 25 | 36.6 | 2 | 6 |
| L-81 | 20 | 43.7 | 2 | 4 |
| L-121 | 14 | 32.5 | 2 | 6 |
| 31 R2 | 30 | 41.2 | 2 | 11 |
| L-35 | 77 | 53.0 | 2 | 5 |
| L-44 | 65 | 48.3 | 2 | 8 |
| L-31 | 37 | 50.4 | 2 | 8 |
| 25 R2 | 33 | 40.1 | 2 | 9 |

All of the "Pluronic" polyols listed in Table XI are "surface active," in this case that is, are able to reduce the surface tension of water. None of the listed materials exhibited a surface tension as a 0.01% aqueous solution at 25° C. above about 55 dynes per centimeter. The "Pluronic" types "P-103"; "P-104"; "P-105"; "F-108"; "F-123" and "F-127" all were excessively soluble for use according to my invention, exhibiting a cloud point in excess of about 80° C. These also exhibited high foaming ability as evidenced by their having a mechanically-induced, agitated foam height value in excess of about 30 millimeters. The polyol "P-84" had a solubility near the 80° C. limit, but was too high a foam producer, showing a foam height in excess of about 30 millimeters according to my test procedure. The preferred "Pluronic" types "L-62"; "L-92"; and "L-72" exhibited cloud points in the range of about 20° to 35° C., and mechanically-induced, agitated foam heights in the range of about 10 to 20 millimeters in the water-alcohol mixture.

EXAMPLE II

In this example, the efficacy of certain synthetic surface active alkyl aryl polyether alcohols as low addition rate, compressive strength-enhancing additives for hydraulic cement compositions is illustrated. In particular, representative results of the effects of certain non-ionic surface active condensation products of octylphenol or nonylphenol with ethylene oxide offered under the commercial names "Triton X" (Rohm & Haas CO), "Igepal Co" (General Aniline & Film Corp), and "Surfonic N" (Jefferson Chemical Co., Inc), upon Portland cement concretes at low addition rates are presented herein.

The "Triton X" non-ionic materials employed herein are well known, commercially available surfactants. They are prepared by condensing octylphenol with a varying number of moles of ethylene oxide. The "Surfonic N" and "Igepal Co" surfactants utilized herein are similarly well known commercially available non-ionic surfactants prepared by condensing nonylphenol with a varying number of moles of ethylene oxide. Hydrophilic character is given to the alkylphenol hydrophobic moiety by the incorporation of the poly (oxyethylene) units. The particular alkyl aryl polyether alcohols mentioned in the experiments of this Example are listed in Table XII below, along with detailed chemical and physical information relevant to my invention and described previously. The representative effect of the addition of these materials on Portland cement concrete air, strength etc. is illustrated in the following Tables XIII-XX. Tests and measurements were performed and taken as in Example I. The foam height values are those as tested in the above described alcohol-water mixture.

TABLE XII

| Alkyl Aryl Polyether Alcohol | % Poly(oxyethylene) in Total Molecule | Cloud PT. (° C) | Surface Tension (Dynes/cm) | Mechanically-induced Agitated Foam Height | |
|---|---|---|---|---|---|
| | | | | No. Tests | Average Foam Height (mm) |
| Triton X-100 | 66–68 | 65 | 31 | 2 | >150 |
| Triton X-114 | 60–63 | 25 | 30 | 2 | 129 |
| Triton X-45 | 51 | >0 | 29 | 2 | 31 |
| Triton X-35 | 39 | >0 | 29 | 2 | 2 |
| Triton X-15 | 18 | >0 | Insol | 1 | 0 |
| Surfonic N-95 | 64–67 | 54.2 | 30.5 | 2 | >150 |
| Surfonic N-60 | 54 | Insol | 28.9 | 2 | 62 |
| Surfonic N-40 | 44 | Insol | 28 (Approx.) | 2 | 5 |
| Surfonic N-20 | 29 | Insol | Insol | 1 | 0 |
| Surfonic N-10 | 17 | Insol | Insol | 1 | 0 |
| Igepal CO-530 | 54 | Insol | 28 (Approx.) | 2 | 45 |
| Igepal CO-520 | 50 | Insol | 30 | 2 | 37 |
| Igepal CO-430 | 44 | Insol | Insol | 2 | 14 |

TABLE XIII

| Alkyl Aryl Polyether Alcohol | W/C | Slump | % Air | COMPRESSIVE STRENGTH - PSI | | |
|---|---|---|---|---|---|---|
| | | | | 1 Day | 7 Days | 28 Days |
| ATLANTIC I CEMENT BATCH A | | | | | | |
| Blank | 0.59 | 4 | 1.3 | 1440 | 3864 | 5586 |
| 0.002% Triton X-35 | 0.57 | 3¾ | 2.1 | 1798 | 4488 | 6028 |
| UNIVERSAL ATLAS INDIANA I CEMENT BATCH B | | | | | | |
| Blank | 0.58 | 4¼ | 1.1 | 1062 | 3366 | 5113 |
| 0.002% Triton X-35 | 0.55 | 4¼ | 2.1 | 1281 | 3856 | 5650 |
| CANADA I CEMENT BATCH C | | | | | | |
| Blank | 0.59 | 4¼ | 1.5 | 1158 | 3291 | 4369 |
| 0.002% Triton X-35 | 0.57 | 4 | 2.2 | 1154 | 3402 | 4480 |
| CANADA I CEMENT BATCH D | | | | | | |
| Blank | 0.55 | 4¼ | 1.4 | 1444 | 3398 | 4389 |
| Blank | 0.56 | 4 | 1.9 | 1214 | 3064 | 4114 |
| 0.004% Triton X-35 | 0.56 | 4 | 2.0 | 1532 | 3816 | 4795 |
| 0.010% Triton X-35 | 0.54 | 4¼ | 2.0 | 1456 | 3478 | 4528 |
| ATLANTIC I CEMENT BATCH E | | | | | | |
| Blank | 0.61 | 4 | 1.4 | 955 | 3016 | 4651 |
| 0.006% Triton X-15 | 0.58 | 3¾ | 2.2 | 891 | 3565 | 5045 |
| 0.006% Triton X-35 | 0.58 | 3¾ | 2.1 | 1011 | 3856 | 5196 |
| 0.006% Triton X-45 | 0.57 | 3¼ | 2.2 | 1046 | 3700 | 5300 |
| 0.006% Triton X-114 | 0.56 | 3¼ | 2.7 | 1023 | 3497 | 5173 |
| 0.006% Triton X-100 | 0.58 | 4¼ | 3.0 | 959 | 3497 | 4922 |
| 0.006% Triton X-100 | 0.57 | 3¼ | 2.5 | 951 | 3609 | 5244 |

TABLE XIV

| Alkyl Aryl Polyether Alcohol | W/C | Slump | % Air | COMPRESSIVE STRENGTH - PSI | | |
|---|---|---|---|---|---|---|
| | | | | 1 Day | 7 Days | 28 Days |
| ATLANTIC I CEMENT BATCH F | | | | | | |
| Blank | 0.61 | 4 | 1.4 | 951 | 3283 | 4914 |
| 0.010% Triton X-15 | 0.59 | 4 | 2.0 | 959 | 3446 | 4994 |
| 0.010% Triton X-35 | 0.58 | 3½ | 2.0 | 991 | 3462 | 5216 |
| 0.010% Triton X-45 | 0.57 | 3½ | 2.4 | 1134 | 3891 | 5419 |
| 0.010% Triton X-114 | 0.56 | 3½ | 3.3 | 1146 | 3748 | 5491 |
| 0.010% Triton X-100 | 0.54 | 3¼ | 4.0 | 1094 | 3673 | 5017 |

TABLE XIV-continued

| | W/C | Slump | % Air | 1 Day | 7 Days | 28 Days |
|---|---|---|---|---|---|---|
| ATLANTIC I CEMENT BATCH G | | | | | | |
| Blank | 0.61 | 4½ | 1.5 | 824 | 2964 | 4544 |
| 0.02% Triton X-15 | 0.58 | 4½ | 2.1 | 979 | 3501 | 5153 |
| 0.02% Triton X-35 | 0.57 | 4 | 2.3 | 1074 | 3772 | 5427 |
| 0.02% Triton X-45 | 0.55 | 4 | 3.6 | 1214 | 3875 | 5364 |
| 0.02% Triton X-114 | 0.50 | 4 | 7.0 | 1043 | 3410 | 4588 |
| 0.02% Triton X-100 | 0.49 | 4½ | 8.0 | 935 | 3108 | 4086 |
| ATLANTIC I CEMENT BATCH H | | | | | | |
| Blank | 0.58 | 3½ | 1.5 | 1432 | 4072 | 5295 |
| 0.05% X-114 | 0.46 | 7½ | 14.0 | 760 | 1990 | 2485 |

TABLE XV

| Alkyl Aryl Polyether Alcohol Triton X-35 | W/C | Slump | % Air | COMPRESSIVE STRENGTH - PSI | | |
|---|---|---|---|---|---|---|
| | | | | 1 Day | 7 Days | 28 Days |
| ATLANTIC I CEMENT BATCH H | | | | | | |
| Blank | 0.61 | 4 | 1.6 | 911 | 3080 | 4608 |
| 0.001% | 0.58 | 4½ | 2.4 | 1011 | 3529 | 5200 |
| 0.001% | 0.57 | 3½ | 2.0 | 923 | 3617 | 5085 |
| 0.002% | 0.59 | 4 | 2.1 | 971 | 3299 | 4942 |
| 0.004% | 0.58 | 4 | 2.1 | 979 | 3517 | 4994 |
| 0.008% | 0.58 | 4½ | 2.1 | 1023 | 3728 | 5272 |
| 0.016% | 0.58 | 3½ | 2.2 | 1074 | 3744 | 5447 |
| 0.032% | 0.57 | 4½ | 2.5 | 919 | 3649 | 5117 |
| ATLANTIC I CEMENT BATCH I | | | | | | |
| | | | | | 3 days | |
| Blank | 0.60 | 4¾ | 1.6 | 895 | 1906 | 4627 |
| 0.01% | 0.58 | 4½ | 2.1 | 975 | 2196 | 5033 |
| 0.05% | 0.58 | 5 | 2.3 | 907 | 2101 | 4846 |
| 0.10% | 0.58 | 5¼ | 2.2 | 931 | 2053 | 4695 |

TABLE XVI

| Alkyl Aryl Polyether Alcohol Triton X-45 | W/C | Slump | % Air | COMPRESSIVE STRENGTH - PSI | | |
|---|---|---|---|---|---|---|
| | | | | 1 Day | 7 Days | 28 Days |
| ATLANTIC I CEMENT BATCH J | | | | | | |
| Blank | 0.61 | 3¾ | 1.6 | 848 | 3346 | 4791 |
| 0.001% | 0.58 | 3¾ | 2.6 | 995 | 3712 | 5276 |
| 0.004% | 0.58 | 3¼ | 2.2 | 1007 | 3370 | 5232 |
| 0.004% | 0.59 | 4½ | 2.2 | 1062 | 3756 | 5431 |
| 0.008% | 0.57 | 3½ | 2.4 | 995 | 3728 | 5296 |
| 0.016% | 0.56 | 4½ | 3.7 | 1043 | 3720 | 4934 |
| 0.016% | 0.55 | 3½ | 3.3 | 1058 | 3923 | 5300 |
| CANADA I CEMENT BATCH K | | | | | | |
| | | 1st. | 2nd* | | | |
| Blank | 0.59 | 4 | | 1.8 | 1031 | 2921 | 4385 |
| 0.001% | 0.58 | 5¼ | | 1.9 | 1114 | 3231 | 4592 |
| 0.001% | 0.57 | 3½ | | 2.0 | 1210 | 3533 | 4870 |
| 0.004% | 0.58 | 3¼ | | 2.0 | 1114 | 3430 | 4803 |
| 0.008% | 0.56 | 5¼ | | 2.5 | 1202 | 3525 | 4834 |
| 0.008% | 0.55 | 4½ | | 2.5 | 1273 | 3617 | 5025 |
| 0.025% | 0.52 | 5¼ | 3½ | 3.4 | 1305 | 3720 | 4950 |
| 0.025% | 0.53 | 4½ | 3½ | 3.9 | 1162 | 3271 | 4389 |
| 0.05% | 0.53 | 2¾ | 2¼ | 3.7 | 1110 | 2009 | 4122 |
| 0.10% | 0.51 | 4½ | 3½ | 6.9 | 987 | 2582 | 3621 |

TABLE XVI-continued

| | | | | | | | |
|---|---|---|---|---|---|---|---|
| 0.10% | 0.53 | 5¼ | 5¼ | 7.5 | — | — | — |

Observer's Notes:
*Higher addition rates such as 0.025 and 0.05 show a severe loss of slump in the first five minutes after discharge from mixer.
The incremental air is proportional to the addition rate.
The effect of W/C on compressive strength is very critical at the higher addition rates such as 0.025%.

TABLE XVII

CANADA I CEMENT BATCH A

| Alkyl Aryl Polyether Alcohol Igepal CO-430 | W/C | Slump | % Air | COMPRESSIVE STRENGTH - PSI 1 Day | 3 Days | 28 Days |
|---|---|---|---|---|---|---|
| Blank | 0.59 | 3¾ | 1.9 | 859 | 1934 | 3497 |
| Blank | 0.60 | 4¼ | 1.6 | 1130 | 2264 | 4329 |
| 0.005% | 0.57 | 3¼ | 2.1 | 1353 | 2706 | 4472 |
| 0.010% | 0.57 | 3¼ | 2.3 | 1357 | 2678 | 4707 |

CANADA I CEMENT BATCH B

| | | | | | 7 Days | |
|---|---|---|---|---|---|---|
| Blank | 0.58 | 4¼ | 1.7 | 1249 | 3239 | 4405 |
| 0.005% | 0.57 | 4¾ | 2.1 | 1417 | 3541 | 4906 |
| 0.010% | 0.56 | 4¼ | 2.5 | 1508 | 3812 | 4699 |

CANADA I CEMENT BATCH C

| Blank | 0.59 | 3¼ | 1.7 | 1233 | 3430 | 4679 |
|---|---|---|---|---|---|---|
| 0.005% | 0.57 | 3½ | 2.2 | 1385 | 3565 | 4771 |
| 0.010% | 0.56 | 4 | 2.5 | 1301 | 3736 | 4902 |

UNIVERSAL ATLAS INDIANA I CEMENT BATCH D

| Blank | 0.60 | 4¼ | 1.4 | 796 | 3458 | 5188 |
|---|---|---|---|---|---|---|
| 0.0025% | 0.57 | 3¼ | 2.0 | 955 | 3935 | 5610 |
| 0.005% | 0.57 | 4 | 2.1 | 931 | 3899 | 5750 |
| 0.01% | 0.57 | 4 | 2.7 | 979 | 3931 | 5459 |

UNIVERSAL ATLAS INDIANA I CEMENT BATCH E

| Blank | 0.61 | 3¼ | 1.3 | 852 | 3386 | 5328 |
|---|---|---|---|---|---|---|
| 0.0025% | 0.58 | 3¼ | 2.1 | 991 | 3828 | 5761 |
| 0.005% | 0.58 | 3¼ | 2.2, 983 | 3903 | 5642 | |
| 0.005% | 0.59 | 4¼ | 2.2 | 947 | 3752 | 5483 |

UNIVERSAL ATLAS INDIANA I CEMENT BATCH F

| Blank | 0.60 | 3¾ | 1.4 | 788 | 3545 | 5097 |
|---|---|---|---|---|---|---|
| 0.005% | 0.58 | 3¼ | 2.3 | 856 | 3645 | 5352 |

TABLE XVIII

ATLANTIC I CEMENT BATCH G

| Alkyl Aryl Polyether Alcohol Igepal CO-430 | W/C | Slump | % Air | COMPRESSIVE STRENGTH - PSI 1 Day | 7 Days | 28 Days |
|---|---|---|---|---|---|---|
| Blank | 0.60 | 4 | 1.5 | 963 | 3271 | 4647 |
| 0.002% | 0.57 | 3¼ | 2.0 | 1198 | 3585 | 4938 |
| 0.004% | 0.57 | 3¾ | 2.0 | 1301 | 3617 | 5208 |
| 0.008% | 0.56 | 3¼ | 2.3 | 1460 | 4031 | 5626 |

ATLANTIC I CEMENT BATCH H

| Blank | 0.60 | 4¼ | 1.4 | 1027 | 3529 | 4978 |
|---|---|---|---|---|---|---|
| 0.002% | 0.60 | 4¼ | 2.2 | 1194 | 3891 | 5224 |
| 0.004% | 0.58 | 3¾ | 2.1 | 1138 | 3891 | 5077 |
| 0.008% | 0.58 | 5 | 2.4 | 1078 | 3780 | 5181 |
| 0.02% | 0.55 | 3¾ | 3.4 | 1154 | 3696 | 5352 |

ATLANTIC I CEMENT BATCH I

| Blank | 0.60 | 4 | 1.4 | 1074 | 3529 | 4902 |
|---|---|---|---|---|---|---|
| 0.008% | 0.57 | 3¼ | 2.2 | 1234 | 3840 | 5077 |

ATLANTIC I CEMENT BATCH J

| Blank | 0.60 | 5 | 1.4 | 863 | 3183 | 4623 |
|---|---|---|---|---|---|---|
| Blank | 0.59 | 3¼ | 1.4 | 1086 | 3788 | 5248 |
| 0.004% | 0.58 | 3¼ | 2.1 | 1086 | 3629 | 5181 |
| 0.008% | 0.57 | 3¼ | 2.4 | 1118 | 3665 | 5177 |

ATLANTIC I CEMENT BATCH K

| Blank | 0.60 | 4 | 1.5 | 987 | 3338 | 4620 |
|---|---|---|---|---|---|---|
| 0.008% | 0.57 | 3 | 2.5 | 1198 | 3852 | 5125 |
| 0.008% | 0.58 | 3¾ | 2.3 | 1241 | 3792 | 4994 |
| 0.02% | 0.56 | 3¼ | 3.6 | 1206 | 3684 | 4850 |
| 0.02% | 0.57 | 3¾ | 3.5 | 1046 | 3573 | 4930 |
| 0.04% | 0.58 | 2¼ | 3.9 | 852 | 3119 | 4206 |

TABLE XIX

ATLANTIC I CEMENT BATCH L

| Alkyl Aryl Polyether Alcohol Igepal | W/C | Slump | % Air | COMPRESSIVE STRENGTH-PSI 1 Day | 7 Days | 28 Days |
|---|---|---|---|---|---|---|
| Blank | 0.60 | 3¼ | 1.6 | 999 | 3493 | 4942 |
| 0.02% CO-430 | 0.55 | 3¼ | 3.3 | 1313 | 3927 | 5451 |
| 0.2% CO-520 | 0.53 | 3¼ | 4.8 | 1472 | 4222 | 5535 |
| 0.02% CO-530 | 0.52 | 4¼ | 6.0 | 1325 | 3856 | 4914 |

ATLANTIC I CEMENT BATCH M

| Blank | 0.58 | 4 | 1.3 | 1176 | 3933 | 5104 |
|---|---|---|---|---|---|---|
| 0.5% CO-520 | 0.52 | 4¾ | 6.0 | 1241 | 3482 | 4454 |
| 0.05% CO-530 | 0.50 | 5¼ | 8.0 | 1136 | 3234 | 3905 |

TABLE XX

ATLANTIC I CEMENT BATCH A

| Alkyl Aryl Polyether Alcohol Surfonic | W/C | Slump | % Air | COMPRESSIVE STRENGTH-PSI 1 Day | 3 Days | 28 Days |
|---|---|---|---|---|---|---|
| Blank | 0.61 | 4¼ | 1.5 | 896 | 1966 | 4548 |
| 0.02% N-10 | 0.58 | 4¾ | 2.8 | 1031 | 2252 | 5117 |
| 0.02% N-20 | 0.59 | 4¾ | 2.0 | 1150 | 2316 | 5324 |
| 0.02% N-40 | 0.57 | 4¾ | 2.4 | 1086 | 2495 | 5407 |
| 0.02% N-60 | 0.54 | 5¼ | 5.3 | 1257 | 2543 | 5316 |
| 0.02% N-95 | 0.51 | 5¼6.5 | 1062 | 2200 | 4556 | |

ATLANTIC I CEMENT BATCH B

| | | | | | 7 Days | |
|---|---|---|---|---|---|---|
| Blank | 0.60 | 3¼ | 1.6 | 999 | 3493 | 4942 |
| 0.02% N-40 | 0.56 | 3 | 2.6 | 979 | 3549 | 5041 |
| 0.02% N-60 | 0.52 | 5¼ | 6.4 | 1174 | 3350 | 5352 |
| 0.02% N-60 | 0.50 | 2¾ | 5.4 | 1313 | 3935 | 5065 |

ATLANTIC I CEMENT BATCH C

| Blank | 0.60 | 3¼ | 1.5 | 1074 | 3501 | 4699 |
|---|---|---|---|---|---|---|
| 0.02% N-40 | 0.58 | 3 | 2.8 | 1225 | 3840 | 4950 |
| 0.02% N-60 | 0.54 | 5¼ | 6.5 | 1289 | 3422 | 4484 |

My experimental work with the "Tritons" leads me to exclude "Triton X-100," "Triton X-114" and "Triton X-45" as low addition rate, strength enhancing additives according to my invention. These higher ethoxylated condensates of octylphenol entrain considerable amounts of air at the higher addition levels within my 0.001 to 0.10 addition rate. This high air entrainment as aforementioned is detrimental to strength enhancement. "Triton X-45" although a marginal performer, is excluded from my invention since my experiments show it has a tendency to entrain air at the higher addition rate within the aforementioned range, although this tendency did not appear to be as great as in the cases of the higher ethoxylated "Triton X-100" and "Triton X-114."

My experimental work with the ethoxylated nonylphenols "Surfonics" and "Igepals" would appear to correspond to my findings with respect to the ethoxylated octylphenols, the "Tritons." Again I found that as the addition rate increased within the 0.001 to 0.10 range, the materials having a percent ethoxylation over about 50, "Surfonic N-60," "Surfonic N-95," "Igepal CO-530" and "Igepal CO-520", showed a tendency to entrain incremental air. As emphasized previously, this tendency is detrimental to compressive strength gain, and can even be so deleterious to strength as to be dangerous, for example should the material be "overdosed" by the concrete preparer.

An examination of the data in Table XII shows all of the polyether condensates of this Example which I employ as low addition rate strength enhancers according to my invention ("Triton X-35"; "X-15"; "Surfonic N-10"; "N-20," "N-40"; and "Igepal CO-430") to be either insoluble, or to have a "cloud point" near zero. While the remaining polyethers excluded from my invention had cloud points beneath the 80° C. maximum, all exhibited excessive foaming properties as indicated by the "mechanically-induced agitated foam heights" of greater than about 30 millimeters, the maximum according to my invention. As expected, "Triton X-45" was marginal in this respect.

The preferred alkyl aryl polyether alcohol condensates according to my invention are "Triton X-35," "Surfonic N-40" and "Igepal CO-430" which contained about 35 to about 50 percent poly (oxyethylene) in the molecule.

EXAMPLE III

In this Example, the effect of the addition of certain synthetic surface active acetylinic glycols and ethoxylated products thereof as low addition rate, compressive strength enhancing materials according to the invention is illustrated. In particular, representative results of the effects of certain synthetic acetylinic glycols and ethoxylated products thereof offered commercially under the name "Surfynol" by Airco Chemicals and Plastics upon Portland cement concrete compositions at low addition rates are presented herein.

The particular "Surfynol" products used herein are listed in Table XXI along with physical and chemical information relevant to the present information. "Surfynol 104" is a non-ionic surface active agent composed of 2,4,7,9-tetramethyl-5 decyn-4,7 diol. It is a tertiary acetylinic glycol. "Surfynol 440" is a non-ionic surface active agent, and is prepared by reacting "Surfynol 104" with alkylene oxide, i.e. ethylene oxide in a mole ratio of 3.5 moles of ethylene oxide per mole of the tetramethyl decyndiol. "Surfynol 465" is also a non-ionic surface active agent prepared by reacting "Surfynol 104" with ethylene oxide, the mole ratio being 10 moles of ethylene oxide per mole of the tetramethyl decyndiol. The concrete test results performed as in the foregoing Examples are given in Table XXII.

All of the "Surfynol" products tested in Table XXII were effective as low addition rate, compressive strength enhancing additives according to my invention. Again, all of the effective materials were surface-active as evidenced by the fact that each lowered the surface tension of water, were either "insoluble" or had a solubility below the 80° C. approximate limit, and were low foamers as evidenced by the low mechanically-induced agitated foam height values (in water-alcohol mixture).

EXAMPLE IV

In this Example, the efficacy of a proprietary commercial synthetic non-ionic surfactant "Plurafac RA-20" offered commercially by the Wyandotte Chemicals Corp. as a low addition rate, compressive strength-enhancing agent according to the invention is illustrated. The "Plurafac" products are described as 100% active, non-ionic biodegradable surfactants of straight chain, primary aliphatic, oxyethylated alcohols. Physical and chemical information pertinent to this invention concerning "Plurafac RA-20" as well as results representative of the performance of the surfactant as a low addition rate, strength enhancing additive as in the foregoing Examples, are presented in Table XXIII.

TABLE XXI

| Acetylinic Glycol | % Poly(oxyethylene) In total Molecule | Cloud Point (°C) | Surface Tension (Dynes/cm) | Mechanically-Induced Agitated Foam Height | |
|---|---|---|---|---|---|
| | | | | No. Tests | Average Foam Height (mm) |
| Surfynol 104 | 0 | Insoluble | 45.1 | 1 | 0 |
| Surfynol 440 | 41 | Insoluble | 44.0 | 1 | 0 |
| Surfynol 465 | 66 | 61 | 44.5 | 2 | 21 |

TABLE XXII

ATLANTIC I CEMENT BATCH A

| Acetylinic Glycol "Surfynol" | W/C | Slump | % Air | COMPRESSIVE STRENGTH - PSI | | |
|---|---|---|---|---|---|---|
| | | | | 1 Day | 7 Days | 28 Days |
| Blank | 0.60 | 4 | 1.5 | 963 | 3271 | 4647 |
| 0.005% 440 | 0.57 | 3¾ | 2.3 | 1146 | 3549 | 4950 |
| 0.005% 465 | 0.56 | 3¼ | 2.3 | 1325 | 3939 | 5240 |
| 0.005% 104 | 0.57 | 3½ | 2.0 | 1210 | 3637 | 5173 |

CANADA I CEMENT BATCH B

| | | | | 3 Days | | |
|---|---|---|---|---|---|---|
| Blank | 0.60 | 4¼ | 1.6 | 1130 | 2264 | 4329 |
| Blank | 0.59 | 3¾ | 1.9 | 859 | 1934 | 3491 |
| 0.01% 440 | 0.57 | 3 | 2.6 | 1210 | 2574 | 4635 |
| 0.01% 465 | 0.57 | 4 | 2.8 | 1186 | 2395 | 4365 |

UNIVERSAL ATLAS INDIANA I CEMENT BATCH C

| | | | | 7 Days | | |
|---|---|---|---|---|---|---|
| Blank | 0.60 | 4¼ | 1.4 | 796 | 3458 | 5188 |
| 0.01% 465 | 0.56 | 3½ | 2.7 | 871 | 3947 | 5395 |
| 0.02% 465 | 0.55 | 3 | 2.9 | 859 | 3899 | 5248 |

IDEAL I CEMENT BATCH D

| Blank | 0.58 | 3½ | 1.6 | 871 | 3382 | 4781 |
| 0.01% 465 | 0.56 | 3¾ | 2.9 | 921 | 3429 | 5091 |
| 0.05% 465 | 0.56 | 3½ | 2.4 | 940 | 3284 | 5208 |
| 0.10% 465 | 0.57 | 4 | 2.3 | 948 | 3476 | 5082 |

TABLE XXIII

| Additive | % Poly (oxyethylene) in Total Molecule | Cloud Point °C) | Surface Tension (Dynes/cm) | Mechanically-Induced agitated Foam Height (mm) | |
|---|---|---|---|---|---|
| | | | | No. Tests | Average Foam Height |
| Plurafac RA=20 | not available | 45 | 32.9 | 2 | 87 |

ATLANTIC L CEMENT BATCH A

| PLURAFAC RA-20 | W/C | Slump | % Air | COMPRESSIVE STRENGTH -PSI | | |
|---|---|---|---|---|---|---|
| | | | | | 1 Day | 7 Days | 28 Days |
| Blank | 0.58 | 3¼ | 1.5 | 1432 | 4072 | 5295 |
| 0.01% | 0.55 | 4 | 3.1 | 1292 | 4117 | 5309 |
| 0.025% | 0.51 | 5 | 7.0 | 1358 | 3651 | 4496 |
| 0.05% | 0.48 | 4¼ | 8.8 | 1381 | 3618 | 4337 |

My results testing the effects of "Plurafac RA-20" as a low addition rate, compressive strength-enhancing additive according to the invention indicate that as the amount of this surfactant is increased in my addition range, very high strength-damaging incremental air is entrained. The surfactant additive lowered the surface tension of water and had a low solubility, but created an amount of foam, 87 millimeters, in excess of the approximate 30 millimeter limit according to my invention.

In another similar experiment testing the effect of "Plurafac RA-40" as a compressive strength-enhancer for Portland cement concrete, this material was found to entrain strength-damaging high amounts of air at an addition rate of 0.05%. "Plurafac RA-40" is a similar synthetic surfactant to "Plurafac RA-20," except that "RA-40" has a cloud point of 25° C. and has a lower degree of ethoxylation than "RA-20" which indicates a lower water solubility. Agitated foam height tests of "Plurafac RA-40" using the method wherein the surfactant is dissolved or dispersed in the water-alcohol mixture indicate a test value of less than 30 millimeters. However, when tested using the procedure wherein the surfactant is dissolved in water alone, "Plurafac RA-40" exhibited a foam height average test value of 38 which is outside of the maximum range.

EXAMPLE V

This Example illustrates the usefulness of small amounts of synthetic block copolymer non-ionic surfactants offered commercially under the name "Tetronic" by the Wyandotte Chemicals Corporation as additives according to the invention. These materials are block copolymer prepared in a manner similar to the "Pluronic" block copolymers of Example 1, except that ethylene diamine is used as the base to which ethylene oxide and propylene oxide are added sequentially. As in the case of the "Pluronics," the products vary depending upon the amount poly (oxypropylene) hydrophobe and the % poly (oxethylene) hydrophilic units present in the molecule. The "Tetronic" block copolymers employed herein are listed in Table XXIV, and the physical and chemical properties thereof relevant to this invention in Table XXV. Tables XXVI and XXVII represent the test results in concrete preformed as in previous Examples.

TABLE XXIV

| "Tetronic" Product Designation | Typical Molecular wt. of poly (oxy propylene) Hydrophobe | % Poly (oxyethylene) Hydrophilic Unit in Total Molecule |
|---|---|---|
| 1502 | 6501–7000 | 20 |
| 1102 | 4501–5000 | 20 |
| 702 | 2501–3000 | 20 |
| 1501 | 6501–7000 | 10 |
| 1301 | 5501–6000 | 10 |
| 1101 | 4501–5000 | 10 |
| 901 | 3501–4000 | 10 |
| 701 | 2501–3000 | 10 |

TABLE XXV

| "Tetronic" Designation | Cloud Point (° C) | Surface Tension (Dynes/cm) | Mechanically-Induced Agitated Foam Height | |
|---|---|---|---|---|
| | | | No. of Tests | Av. Foam Ht. (mm) |
| 1502 | 70 | 35 (estimated) | 2 | 44 |
| 1102 | 31 | 36 (estimated) | 2 | 29 |
| 702 | 27 | 41.1 | 3 | 5 |
| 1501 | 15 | 35.1 | 2 | 3 |
| 1301 | 16 | 34.7 | 3 | 9 |
| 1101 | 17 | 35.7 | 1 | 0 |
| 901 | 20 | 37.3 | 1 | 0 |
| 701 | 22 | 40.9 | 1 | 0 |

TABLE XXVI

| | | | | COMPRESSIVE STRENGTH -PSI | | |
|---|---|---|---|---|---|---|
| "Tetronic" Polyol | W/C | Slump | % Air | 1 Day | 7 Days | 28 Days |
| CANADA I CEMENT BATCH A | | | | | | |
| Blank | 0.60 | 4½ | 1.5 | 1082 | 3250 | 4110 |
| 0.01% 901 | 0.58 | 5¼ | 2.1 | 1210 | 3438 | 4687 |
| 0.01% 1101 | 0.58 | 3½ | 2.0 | 1261 | 3525 | 4154 |
| 0.01% 1301 | 0.58 | 3½ | 2.0 | 1154 | 3342 | 4417 |
| 0.01% 1501 | 0.58 | 4½ | 1.9 | 1122 | 3330 | 4369 |
| 0.01% 1102 | 0.57 | 5¾ | 3.1 | 1078 | 3414 | 4230 |
| 0.01% 1102 | 0.55 | 4¾ | 2.9 | 1142 | 3390 | 4405 |
| 0.01% 1502 | 0.58 | 4 | 1.9 | 1074 | 3430 | 4381 |
| CANADA I CEMENT BATCH B | | | | | | |
| Blank | 0.60 | 5 | 1.5 | 1214 | 3501 | 4803* |
| 0.02% 701 | 0.59 | 4 | 1.8 | 1146 | 3219 | 4440 |
| 0.02% 1101 | 0.59 | 4 | 1.6 | 1409 | 3414 | 4504 |
| 0.02% 1301 | 0.58 | 4½ | 2.0 | 1234 | 3450 | 4616 |
| 0.02% 1501 | 0.59 | 4½ | 1.7 | 1202 | 3458 | 4584 |
| 0.02% 702 | 0.57 | 3½ | 2.2 | 1253 | 3513 | 4810 |
| 0.02% 1102 | 0.57 | 6¾ | 4.9 | 1110 | 3255 | 4238 |
| 0.02% 1502 | 0.58 | 3¾ | 1.9 | 1222 | 3583 | 4830 |

*Experimenter's Note: Unusually high compressive strength value for a blank of this brand and type of cement. Results of experiment questionable.

TABLE XXVII

| | | | | COMPRESSIVE STRENGTH -PSI | |
|---|---|---|---|---|---|
| Tetronic Polyol | W/C | Slump | % Air | 1 Day | 7 Days |
| ATLANTIC I CEMENT BATCH C | | | | | |
| Blank | 0.59 | 4 | 1.6 | 986 | 3388 |
| 0.05% 701 | 0.58 | 4¼ | 1.7 | 1097 | 3514 |
| 0.05% 901 | 0.57 | 4¼ | 1.8 | 1210 | 3855 |
| 0.05% 1101 | 0.57 | 3¾ | 1.7 | 1137 | 3611 |
| 0.05% 1301 | 0.56 | 3½ | 2.4 | 1168 | 3761 |
| 0.05% 1501 | 0.57 | 3¾ | 1.7 | 1160 | 3725 |
| 0.05% 702 | 0.57 | 3¾ | 2.2 | 1055 | 3389 |
| 0.05% 1102 | 0.51 | 5 | 7.5 | 1099 | 3185 |
| 0.05% 1502 | 0.52 | 3¾ | 5.8 | 1162 | 3266 |
| ATLANTIC I CEMENT BATCH D | | | | | |
| 0.05% 702 | 0.56 | 3½ | 2.4 | No cylinders Cast | |
| 0.05% 1102 | 0.53 | 5¾ | 7.2 | No cylinders Cast | |
| 0.05% 1502 | 0.53 | 3¾ | 6.0 | No cylinders Cast | |

My experiments with the "Tetronic" type block copolymers listed in Tables XXIV and XXV lead me to exclude those designated as "1102" and "1502." As the addition rate was increased to 0.05%, these additives showed a tendency to entraine large amounts of incremental air, which as my previous experiments have shown, usually offsets any strength gain, or even results in a net loss of strength as compared to the blank at 28 days.

EXAMPLE VI

In this Example, representative results are given of only preliminary evaluations I have made of commercially available synthetic surfactants in addition to those of Examples I–V as low addition rate, strength-enhancing additives for hydraulic cement compositions.

The results of an experiment involving the addition of small amounts of certain non-ionic, surface active polyethylene glycol esters offered commercially under the name "ARMAK KESSCO PEG" by Armour Industrial Chemical Co. are given in Table XXVIII. The materials shown are polyoxyethylene esters of oleic acid. The number following the "PEG" in the Table indicates the molecular weight of the polyoxyethylene glycol portion of the molecule.

TABLE XXVIII
ATLANTIC I CEMENT BATCH

| Polyethylene Glycol Ester (Di-oleate) | | W/C | Slump | % Air | COMPRESSIVE STRENGTH -PSI | | |
|---|---|---|---|---|---|---|---|
| | | | | | 1 Day | 7 Days | 28 Days |
| Blank | | 0.59 | 3¾ | 1.4 | 1154 | 3406 | 4926 |
| 0.001 | PEG 200 | 0.57 | 3¾ | 1.7 | 1305 | 3752 | 5073 |
| 0.01 | PEG 200 | 0.56 | 4 | 2.0 | 1313 | 3796 | 4814 |
| 0.001 | PEG 400 | 0.57 | 4¼ | 2.2 | 1325 | 3708 | 5065 |
| 0.01 | PEG 400 | 0.56 | 4¼ | 2.9 | 1206 | 3478 | 4655 |
| 0.001 | PEG 600 | 0.57 | 3¾ | 1.9 | 1373 | 3907 | 5244 |
| 0.01 | PEG 600 | 0.55 | 4 | 2.8 | 1245 | 3597 | 4759 |
| 0.05 | PEG 400 | 0.58 | 2½ | 2.7 | 1070 | 3115 | 4643 |

Other commercially available surface active products that I have also tested as low addition rate strength-enhancing additives for Portland cement concrete in the manner of the previous Examples included (a) "BRIJ 92" (Atlas Chemical Industries, Inc.) a non-ionic polyoxyethylene ether of oleyl alcohol which when added at 0.02% exhibited increase in compressive strength of the concrete; "BRIJ 30" (Atlas Chemical Industries, Inc.) a non-ionic polyoxyethylene ether of lauryl alcohol which at the 0.02% addition level tended to entrain a high amount of incremental air which discouraged further testing, and "BRIJ 72" (Atlas Chemical Industries, Inc.) a non-ionic polyoxyethylene ether of stearyl alcohol which when added at the 0.02% level exhibited the same tendencies as "BRIJ 30", (b) "SPAN 80" (Atlas Chemical Industries, Inc.) a non-ionic fatty acid partial ester of sorbitol anhydride (sorbitan monooleate) which when added at a level of 0.02% caused high incremental air entrainment and low compressive strength; (c) "TWEEN 81" (Atlas Chemical Industries, Inc.) a non-ionic polyoxyethylene derivative of a fatty acid partial ester of sorbitol anhydride (polyoxyethylene 5 sorbitan monooleate), which, at a 0.02% addition level entrained a moderate amount of incremental air and exhibited a slightly lower compressive strength than the blank; (d) "TERGITOL 15-S-3" (Union Carbide Corp.) a non-ionic polyethylene glycol ether of a linear alcohol which when added at a 0.02% addition level entrained a low amount of incremental air and exhibited a compressive strength increase; "TERGITOL 15-S-5" (Union Carbide Corp.) a non-ionic polyethylene glycol ether of a linear alcohol having a higher degree of ethoxylation than "TERGITOL 15-S-3" which when added at a level of 0.02% entrained a moderately high amount of incremental air and exhibited a slight compressive strength increase; "TERGITOL 15-S-7," a non-ionic polyethylene glycol ether of a linear alcohol having a higher degree of ethoxylation than "TERGITOL 15-S-3" and "15-S-5" and which at a 0.02% additive rate entrained a high amount of incremental air and exhibited a low compressive strength; (e) "TRITON H-66" (Rohm & Haas Co.) an anionic phosphate ester of an ethoxylated alkylphenol, potassium salt, which at a low addition level entrained high amount of incremental air and exhibited low compressive strength; (f) "TRITON H-55" (Rohm & Hass Co.) an anionic phosphate ester of an ethoxylated alkylphenol, potassium salt, which at a low addition level entrained no incremental air and exhibited a compressive strength increase, and (g) "GAFAC RM-410" (General) Aniline & Film Corporation) an anionic free acid of a complex organic phosphate ester which at an addition rate of 0.05% entrained a moderate amount of incremental air and exhibited a low compressive strength; and (h) "ZONYL" (DuPont) fluorosurfactants, which included "ZONYL FSP," "FSN," "FSB," anionic, nonionic and amphoteric surfactants, all of which exhibited a tendency to entrain incremental air at low addition rates.

Since my low addition rate, compressive strength enhancing surfactant additives have low water-solubility as indicated by low cloud points, I prefer to include a small amount of a solubility-enhancing surfactants such as "TRITON X-100" described above, to assist in solubilizing the surfactant additive of the invention. Such solubilizing action is most helpful in preventing the normally low-solubility strength-increasing surfactant additive of the invention from separating out as a visible separate phase, for instance as ambient temperatures surrounding the product increase.

EXAMPLE VII

The following is a detailed Example of a set-accelerating, strength-enhancing additive composition according to the invention employing a preferred strength-enhancing surfactant of the invention, "Pluronic L-92" described above. The composition is an aqueous blend containing the following porportions of solid materials:

| | Solids % by weight |
|---|---|
| Calcium chloride | 94.60 |
| "Pluronic L-92" | 1.00 |
| "Triton X-100" | 0.40 |
| "Amine" | 4.00 |
| | 100.00 |

A typical addition rate of this additive composition to structural Portland cement concretes lies generally in the range of from about 0.10 to about 2%, preferably about 0.3 to about 1% by weight of additive solids based upon cement solids. The amine used in the above composition was a mixture of alkanolamines and higher boiling homologs obtained as a coproduct in a continuous commercial process of producing amines.

In an experiment, the components of the additive composition detailed above in Example VII were tested singly and in various combinations as additive to Portland cement concretes. Water to cement ratio, slump, % air and compressive strength were all determined as in previous tests, except that the concrete was prepared at 60° F. and cured at 50° F. for three days. The rest of the curing period was at 73° plus or minus 3° F. in a fog room. The concrete cement content was 517 pounds/yard. The test simulates "low temperature" conditions. Setting time was determined according to ASTM C-403. The results shown in Table XXIX below evidence the excellent set acceleration and optimum 3, 7 and 28 day compressive strength enhancement obtained using the combination additive composition of the invention. The results of similar experiments are shown in Table XXX below. In Table XXX, compressive strength gain and set acceleration comparable to higher amounts of calcium chloride are noted.

TABLE XXIX
Ideal I Cement

| CaCl₂ | Amine | % s/s Pluronic L-92 | Triton X-100 | W/C | Slump | % Air | Compressive Strength-PSI 3 Days | 7 Days | 28 Days | INITIAL SET Hours:Mins |
|---|---|---|---|---|---|---|---|---|---|---|
| — | — | — | — | 0.57 | 4¼ | 1.4 | 1148 | 2528 | 4228 | 10:30 |
| 0.473 | — | — | — | 0.57 | 4¼ | 1.9 | 1678 | 3535 | 4865 | 5:55 |
| — | 0.02 | — | — | 0.55 | 4¼ | 1.8 | 1568 | 3202 | 5010 | 6:40 |
| 0.473 | — | 0.005 | — | 0.54 | 4 | 2.9 | 2027 | 3980 | 5220 | 5:30 |
| 0.473 | — | — | 0.002 | 0.56 | 5 | 2.8 | 1800 | 3653 | 4779 | 5:35 |
| 0.473 | 0.02 | — | — | 0.56 | 4¼ | 2.1 | 1890 | 3732 | 5153 | 5:35 |
| 0.473 | 0.02 | 0.005 | 0.002 | 0.53 | 4¾ | 4.2 | 2090 | 4052 | 5426 | 5:30 |

TABLE XXX
Atlantic Cement

| CaCl₂ | % s/s Pluronic L-92 | Triton X-100 | Amine | W/C | Slump | % Air | Compressive Strength-PSI 3 Days | 7 Days | 28 Days | INITIAL SET Hours:Mins |
|---|---|---|---|---|---|---|---|---|---|---|
| — | — | — | — | 0.56 | 3¾ | 1.3 | 1571 | 3038 | 4690 | 8:40 |
| 0.4871 | 0.009 | 0.0039 | — | 0.52 | 3¼ | 3.7 | 2373 | 4324 | 5662 | 5:50 |
| 0.4771 | 0.009 | 0.0039 | 0.01 | 0.52 | 3 | 3.0 | 2681 | 4674 | 5992 | 5:10 |
| 0.7306 | 0.0135 | 0.0059 | — | 0.52 | 6¼ | 9.0 | 2056 | 3766 | 4721 | — |
| 0.7306 | 0.0135 | 0.0059 | — | 0.51 | 1¼ | 2.9 | 2904 | 5048 | 6333 | 4:25 |
| 1.0 | — | — | — | 0.56 | 3¼ | 1.9 | 2469 | 4294 | 5512 | 4:20 |
| 1.5 | — | — | — | 0.57 | 3¼ | 1.7 | 2508 | 4492 | 5436 | 3:25 |
| — | — | — | — | 0.57 | 4 | 1.5 | 1470 | 3019 | 4660 | 8:55 |
| 0.4871 | 0.009 | 0.0039 | — | 0.53 | 5 | 4.4 | 2200 | 4220 | 5363 | 5:50 |
| 0.4771 | 0.009 | 0.0039 | 0.01 | 0.53 | 4¼ | 4.2 | 2375 | 4351 | 5572 | 5:15 |
| 0.7306 | 0.0135 | 0.0059 | — | 0.52 | 6¾ | 8.3 | 2079 | 3995 | 4915 | 5:00 |
| 1.0 | — | — | — | 0.57 | 3¼ | 1.6 | 2246 | 4309 | 5533 | 4:15 |
| 1.5 | — | — | — | 0.58 | 4¼ | 1.5 | 2416 | 4500 | 5637 | 3:25 |

In Table XXXI below, the effect of varying the amine concentration in the composition of the invention is shown. In Table XXXII, the effect of varying the amount of "Pluronic L-92" is shown, as in a comparison between a composition of the invention containing a smaller amount of calcium chloride and an ASTM TYPE A C494 water reducing admixture containing additionally, 1 percent of calcium chloride.

In Table XXXIII to XXXV below, the effect of varying the addition rate of the composition of the invention is shown.

TABLE XXXI
Atlantic 1 cement

| CaCl₂ | % s/s Pluronic L-92 | Triton X-100 | Amine | W/C | Slump | % Air | Compressive Strength-PSI 3 Days | 7 Days | 28 Days | INITIAL SET Hours:Mins |
|---|---|---|---|---|---|---|---|---|---|---|
| — | — | — | — | 0.57 | 4 | 1.6 | 1441 | 3391 | 4755 | 9:00 |
| 0.483 | 0.005 | 0.002 | 0.01 | 0.55 | 4 | 3.1 | 2186 | 4280 | 5522 | 5:45 |
| 0.473 | 0.005 | 0.002 | 0.02 | 0.54 | 4 | 3.2 | 2411 | 4656 | 5925 | 5:30 |

TABLE XXXIIO
Atlantic 1 Cement

| CaCl₂ | % s/s Pluronic L-92 | Triton X-100 | Amine | W/C | Slump | % Air | Compressive Strength-PSI 3 Days | 7 Days | 28 Days | INITIAL SET Hours:Mins |
|---|---|---|---|---|---|---|---|---|---|---|
| — | — | — | — | 0.57 | 4 | 1.6 | 1441 | 3391 | 4755 | 9:00 |
| 0.480 | 0.007 | 0.003 | 0.01 | 0.54 | 3¾ | 3.0 | 2344 | 4469 | 5562 | 5:40 |
| 0.483 | 0.005 | 0.002 | 0.01 | 0.55 | 4 | 3.1 | 2186 | 4280 | 5522 | 5:45 |
| — | — | — | — | 0.57 | 4 | 1.6 | 1441 | 3391 | 4755 | 9:00 |
| 0.473 | 0.005 | 0.002 | 0.02 | 0.54 | 4 | 3.2 | 2411 | 4656 | 5925 | 5:30 |
| 0.720 | 0.0105 | 0.0045 | 0.015 | 0.52 | 4¼ | 4.8 | 2576 | 4763 | 5981 | 4:45 |
| 1.0 | and ASTM C494 Type A Admixture | | | 0.54 | 3 | — | 2650 | 4865 | 6039 | 4:40 |

TABLE XXXIII
Ideal 1 Cement

| CaCl₂ | % s/s Pluronic L-92 | Triton X-100 | Amine | W/C | Slump | %Air | Compressive Strength-PSI 3 Days | 7 Days | 28 Days | INITIAL SET Hour:Mins |
|---|---|---|---|---|---|---|---|---|---|---|
| — | — | — | — | 0.57 | 4 | 1.7 | 1190 | 2518 | 4389 | 9:35 |
| 0.473 | 0.005 | 0.002 | 0.02 | 0.54 | 4 | 3.2 | 2001 | 3610 | 5205 | 6:15 |
| 0.710 | 0.0075 | 0.003 | 0.03 | 0.53 | 4 | 3.9 | 2228 | 3992 | 5451 | 5:10 |
| 0.946 | 0.010 | 0.004 | 0.04 | 0.52 | 3¾ | 4.4 | 2494 | 4283 | 5849 | 4:15 |

TABLE XXXIV

Atlantic 1 Cement

| CaCl$_2$ | % s/s Pluornic L-92 | Triton X-100 | Amine | W/C | Slump | %Air | Compressive Strength-PSI 3 Days | 7 Days | 28 Days | INITIAL SET Hours:Mins |
|---|---|---|---|---|---|---|---|---|---|---|
| — | — | — | — | 0.57 | 4 | 1.7 | 1704 | 3135 | 4659 | 10:05 |
| 0.3784 | 0.004 | 0.0016 | 0.016 | 0.55 | 4¼ | 2.7 | 2523 | 4148 | 5467 | 6:40 |
| 0.5676 | 0.006 | 0.0024 | 0.024 | 0.54 | 4 | 2.9 | 2698 | 4442 | 5724 | 6:25 |
| 0.7568 | 0.008 | 0.0032 | 0.032 | 0.53 | 4 | 3.4 | 3005 | 4503 | 5934 | 6:00 |

TABLE XXXV

Ideal 1 Cement

| CaCl$_2$ | Pluronic L-92 | % s/s Triton X-100 | Amine | W/C | Slump | % Air | Compressive Strength-PSI 3 Days | 7 Days | 28 Days |
|---|---|---|---|---|---|---|---|---|---|
| — | — | — | — | 0.57 | 4¼ | 1.4 | 1104 | 2607 | 4477 |
| 0.0946 | 0.001 | 0.0004 | 0.004 | 0.55 | 4¼ | 2.1 | 1510 | 3150 | 4923 |
| 0.1892 | 0.002 | 0.0008 | 0.008 | 0.55 | 3½ | 2.7 | 1690 | 3366 | 5114 |
| 0.2838 | 0.003 | 0.0012 | 0.012 | 0.55 | 3½ | 2.8 | 1913 | 3541 | 5312 |

It is claimed:

1. A set-accelerating, compressive strength-enhancing additive composition for hydraulic cement compositions, said additive composition consisting essentially of (a) a major amount of a chloride, formate or nitrite salt set-accelerating agent or mixture thereof, (b) from about 1 to about 6 percent by weight of an amine, and (c) from about 0.15 to about 3 percent by weight of a synthetic surface active agent having the following characteristics:
   (1) a cloud point as defined herein not exceeding about 80° centigrade; and (2) a mechanically-induced agitated foam height as defined herein of less than about 30 millimeters.

2. The composition of claim 1 wherein said set accelerating agent is calcium chloride.

3. The composition of claim 1 wherein said surface active agent is non-ionic and is selected from the group consisting of (a) alkyl aryl polyether alcohols; (b) block copolymers of alkylene glycols or alkylene diamines with propylene oxide and ethylene oxide; (c) acetylinic glycols and reaction products thereof with alkylene oxides; (d) and mixtures thereof.

4. The composition of claim 1 wherein said amine is an alkanol amine or mixture of such.

5. The composition of claim 1 additionally containing a small amount of the condensation product of octylphenol with sufficient ethylene oxide to give in excess of 50 percent poly(oxyethylene) in the total molecule, said amount being sufficient to render said component, more soluble in water and thereby prevent such component from separating out from an aqueous mixture containing such additive composition.

6. The composition of claim 1 wherein said surface active agent exhibits a surface tension as a 0.01% aqueous solution at 25° C. of less than about 55 dynes per centimeter.

7. The composition of claim 1 wherein said surface active agent is a block copolymer of an alkylene glycol and one or more alkylene oxides.

8. The composition of claim 1 wherein said surface active agent is a block copolymer prepared by adding either propylene oxide and then ethylene oxide, or ethylene oxide followed by propylene oxide to ethylene glycol.

9. The composition of claim 8 wherein said surface active agent possesses a said "cloud point" in the range of about 20° to 35° C. and a said foam height in the range of about 10 to 20 millimeters.

10. The composition of claim 8 wherein said surface active agent is prepared by adding propylene oxide followed by ethylene oxide to propylene glycol and further wherein (a) the molecular weight of the poly (oxypropylene) portion of the copolymer ranges from about 950 to about 1750, and the percent poly (oxyethylene) portion in the total copolymer molecule is from about 10 to about 50; (b) said molecular weight is from about 1750 to about 2750 and said percent poly (oxyethylene) is from about 10 to about 30; or (c) said molecular weight is from about 2750 to about 4000 and said percent poly (oxyethylene) is from about 10 to about 20.

11. The composition of claim 10 wherein said molecular weight ranges from about 1450 to about 3000, and said percent poly (oxyethylene) is between about 15 to about 35.

12. The composition of claim 8 wherein said surface active agent is prepared by adding ethylene oxide followed by propylene oxide to propylene glycol and (a) the molecular weight of the poly (oxypropylene) portion is about 2500 and the percent poly (oxyethylene) units in the total copolymer molecule is in the range of about 10 to 80, or (b) said molecular weight of the said poly (oxypropylene) portion is about 3100 and said poly (oxyethylene) units is about 10 to 40.

13. The composition of claim 1 wherein said surface active agent is a non-ionic alkyl aryl polyether alcohol.

14. The composition of claim 13 wherein said polyether alcohol is a condensation product of an alkylphenol with ethylene oxide.

15. The composition of claim 14 wherein said condensation product has less than about 50 percent poly (oxyethylene) in its total molecule.

16. The composition of claim 15 wherein the percent poly (oxyethylene) in the total molecule is in the range of from about 35 to about 50.

17. The composition of claim 1 wherein said surface active agent is a non-ionic acetylinic glycol or an alkoxylated product thereof.

18. The composition of claim 17 wherein said surface active agent is a tertiary acetylinic glycol.

19. The composition of claim 18 wherein said glycol is 2,4,7,9-tetramethyl-5-decyn-4,7 diol.

20. The composition of claim 17 wherein said surface active agent is a reaction product of ethylene oxide and said acetylinic glycol.

21. The composition of claim 20 wherein said product contains 3.5 to 10 moles of ethylene oxide per mole of acetylinic glycol.

22. The composition of claim 1 wherein said surface active agent is a block copolymer of ethylene diamine, ethylene oxide and propylene oxide.

23. The composition of claim 22 wherein the molecular weight of the poly (oxypropylene) portion of said copolymer ranges from about 2500 to about 4500 and the percent poly (oxyethylene) units in the total polymer molecule ranges between about 10 up to about 20.

24. A hydraulic cement composition consisting essentially of a hydraulic cement and from about 0.10 to about 2 percent by weight based upon said cement of the additive composition according to claim 1.

25. The composition of claim 24 wherein said cement is Portland cement.

26. The composition of claim 24 to which is added water sufficient to give a water to cement ratio of from about 0.4 to 0.6.

27. The composition of claim 24 wherein said cement is a structural concrete composition possessing a compressive strength as measured after 28 days of hydration in excess of 2000 p.s.i.

* * * * *